United States Patent [19]

Prather et al.

[11] Patent Number: 5,998,215
[45] Date of Patent: Dec. 7, 1999

[54] PORTABLE ANALYZER FOR DETERMINING SIZE AND CHEMICAL COMPOSITION OF AN AEROSOL

[75] Inventors: Kimberly A. Prather; Joseph E. Mayer, both of Riverside, Calif.

[73] Assignee: The Regents of the University of California, Oakland, Calif.

[21] Appl. No.: 08/943,760

[22] Filed: Oct. 3, 1997

Related U.S. Application Data

[63] Continuation-in-part of application No. 08/435,109, May 1, 1995, Pat. No. 5,681,752.

[51] Int. Cl.$^6$ .......................... G01N 24/00; B01D 59/44; H01J 49/00

[52] U.S. Cl. .......................... 436/173; 436/183; 250/281; 250/282; 250/286; 250/287; 250/288; 250/289

[58] Field of Search ........................ 436/173, 183; 250/281–282, 286–289, 396 R

[56] References Cited

U.S. PATENT DOCUMENTS

| | | | |
|---|---|---|---|
| 3,727,047 | 4/1973 | Janes | 250/287 X |
| 3,854,321 | 12/1974 | Dahneke | 73/28 |
| 4,358,302 | 11/1982 | Dahneke | 55/392 |
| 4,383,171 | 5/1983 | Sinha | 250/282 |
| 4,625,112 | 11/1986 | Yoshida | 250/287 |
| 4,694,168 | 9/1987 | Le Beyec et al. | 250/287 |
| 5,382,794 | 1/1995 | Downey et al. | 250/288 |
| 5,681,752 | 10/1997 | Prather | 436/173 |

FOREIGN PATENT DOCUMENTS

| | | |
|---|---|---|
| 4331002 | 3/1995 | Germany . |
| 59-99352 | 6/1984 | Japan . |
| 60-93944 | 5/1985 | Japan . |

OTHER PUBLICATIONS

J.J. Stoffels *Int. J. Mass Spectrom. Ion Phys*, 1981, 40, 217–222.

D.M. Lubman et al, *Anal, Chem.* 1983, 55, 1437–1440.

A. Lieberman etal. "Aerosols Min. Ind. Work Environ." 1983, vol. 3, V.A. Marple et al. Ed., Ann Arbor Sci: Ann Arbor, Michigan, 811–824.

(List continued on next page.)

*Primary Examiner*—Arlen Soderquist
*Attorney, Agent, or Firm*—Sheppard, Mullin, Richter & Hampton LLP; James R. Brueggemann

[57] ABSTRACT

A portable analyzer for determining the size and chemical composition of particles suspended in an aerosol. The aerosol is accelerated through a nozzle and skimmers, to produce a well-defined beam of particles, the speed of which is inversely related to the particle size. A dual-beam laser system positioned along the beam path detects light scattered from each particle, to determine the particle's velocity and thus its aerodynamic size. The laser system also triggers a laser to produce a beam that irradiates the particle, to desorb it into its constituent molecules. The particle is desorbed in a source region of a bipolar, time-of-flight mass spectrometer, which provides a mass-to-charge spectrum of the desorbed molecule, thereby chemically characterizing the material of the particle. Several structural features provide sufficient ruggedness to allow the analyzer to be easily used in the field with minimum calibration and maintenance.

27 Claims, 11 Drawing Sheets

OTHER PUBLICATIONS

M. P. Sinha *Rev. Sci. Instrum.* 1984, 55, 886–891.
T. Bergmann et al. *Rev. Sci. Instrum.* 1990, 61, 2592–2600.
P.J. McKeown et al. *Anal. Chem,* 1991, 63, 2069–2073.
F.H. Strobel et al, *Anal, Chem.* 1992, 64, 754–762.
W.D. Reents Jr. et al. *Plasma Sources Sci. Technol.* 1994, 3, 369–372.
T.J. Cornish et al. *Rapid Commun. Mass Spectrom.* 1994, 8, 781–785.
M. Yang et al. *Proc. SPIE–Int. Soc. Opt. Eng,* 1995, 2385, 51–58.
K.R. Nuebauer et al. *Int. J. Mass Spectrom. Ion Processes* 1995, 151, 77–87.
W.A. Bryden et al, *Proc. SPIE–Int. Soc. Opt. Eng.* 1995, 2511, 153–164.
D.M. Murphy et al. *Aerosol Sci. Technol.* 1995, 22, 237–249.
K.–P. Hinz et al. *Aerosol Sci. Technol,* 1996, 24, 233–242.
M. Weiss et al. *J. Aerosol Sci.* 1997, 28, 159–171.
E. Gard et al. *Anal. Chem.* 1997, 69, 4083–4091.
Dahneke, B., "Sampling and Analysis of Suspended Particles and Vapors by Continuum Source Particle Beams," The American Institute of Chemical Engineers, pp. 134–143, 1980.
Allen, J. et al., "Mass Spectrometric Analyzer of Individual Aerosol Particles," American Institute of Physics, pp. 804–809, Jun. 1981.

Marijnissen, J. et al., "Proposed On–Line Aerosol Analysis Combining Size Determination Laser–Induced Fragmentation and Time–Flight Mass Spectroscopy," J. Aerosol Sci., vol. 19, No. 7, pp. 1307–1310, 1988.

Kievit, O., et al., "On–Line Measurement of Particle Size and Composition," J. Aerosol Sci., vol. 23, Supple. 1, pp. S301–S304, 1992.

Fincke, J.R. et al., "Plasma Spraying of Alumina: Plasma and Particle Flow Fields," Plasma Chemistry and Plasma Processing, vol. 13, No. 4, pp. 579–600, 1993.

Nordmeyer T. et al., "Real–Time Measurement Capabilities Using Aerosol Time–of–Flight mass Spectrometry," Analytical Chemistry, vol. 66, No. 20, Oct. 15, 1994, 3540–3542.

Prather, K. et al., "Real–Time Characterization of Individual Aerosol Particles Using Time–of–Flight Mass Spectrometry," Analytical Chemistry, vol. 66, No. 9, May 1, 1994, 1403–1407.

Johnston, M. et al., "MS of Individual Aerosol Particles," Analytical Chemistry, pp. 721–726, Dec. 1, 1996.

Noble, C. et al., "Aerosol Characterization Using Mass Spectrometry," Trends in Analytical Chemistry, vol. 13, No. 5, 1994, 218–222.

PORTABLE ANALYZER FOR DETERMINING SIZE AND CHEMICAL COMPOSITION OF AN AEROSOL

RELATED APPLICATION

This is a continuation-in-part of Ser. No. 08/435,109, filed May 1, 1995, now U.S. Pat. No. 5,681,752.

FIELD OF THE INVENTION

The invention relates generally to aerosol analyzers. In particular, the invention relates to apparatus for determining the size and chemical composition of particles suspended in an aerosol utilizing a combination of an optical particle detector and a mass spectrometer.

BACKGROUND ART

An aerosol is a combination of a gas and fine solid particles or liquid droplets suspended in the gas. It has been recognized that many environmental, medical, and industrial problems involve the chemistry of aerosols.

In the case of deleterious environmental effects, it is now known that the particulates suspended in the atmosphere can catalyze reactions in processes that depend both upon the size and the chemical composition of the particles. Modeling of atmospheric processes will require this complete characterization of a complex heterogeneous aerosol.

In the case of deleterious medical effects, many environments contain excessively high amounts of particles, such as coal dust or the like. Although many of the biochemical reactions have been established, the introduction of these particles into the body through the lungs is dependent upon the size of the particles.

In a real environment, the suspended particles are non-uniform, having a range of sizes and compositions. That is, the aerosol is polydisperse with particles. Furthermore, the particle concentration may be relatively low and not be amenable to many characterization techniques. Nonetheless, it is highly desirable to be able to measure both the size and chemical composition of particles in a polydisperse sample. It is also highly desirable that the characterization be performed in situ, allowing for an immediate determination of the aerosol's characteristics.

One of the present inventors in the parent application, incorporated herein by reference in its entirety, has disclosed a novel and useful analyzer capable of in situ analysis of both the size of particles and of their chemical composition. This technology has been reported also by: (1) Prather et al. in AReal-time characterization of individual aerosol particles using time-of-flight mass spectrometry,@ *Analytical Chemistry*, vol. 66, no. 9, 1994, pp. 1403–1407; and (2) Nordmeyer et al. in AReal-time measurement capabilities using aerosol time-of-flight mass spectrometry,@ *Analytical Chemistry*, vol. 66, no, 20, pp. 3540–3542. The analyzer includes two separate but interoperative parts. A first, sizing part 10, as illustrated in the schematic block diagram of FIG. 1, includes an aerosol generator 12, which in the case of environmental testing system may include only a tubular port to the gaseous environment being tested. For other applications, the aerosol generator 12 may include means for converting the substance being tested into an aerosol.

An aerosol interface 14 receiving the output of the aerosol generator 12 includes a nozzle and one or more skimmers between respective differentially pumped vacuum stages which convert the generally isotropic aerosol into a well defined beam of the aerosol environment with the velocity of the entrained particles being dependent upon the size of the those particles entrained within the aerosol. A preferred embodiment of the aerosol interface 14, as explained in the parent application, includes a nozzle through which the aerosol is supersonically accelerated with the particles entrained in the gas. The nozzle is conically shaped with a small aperture in its tip facing downstream. Because of the rapid acceleration, the resultant velocity of the entrained particles is inversely related to the size of those particles, that is, upon the aerodynamic size of the particles. The skimmers are also conically shaped but with their tips facing upstream. They act to remove most of the air or other gas from the particle beam, thereby allowing an open path between atmosphere and the very low vacuum of the mass spectrometer and to create a well defined beam.

This beam of particles is incident upon a dual-laser tracking system 16 which includes two laser particle detectors arranged along the path of the accelerated particles. Each particle in passing the two laser detectors produces a precisely defined electrical pulse. A timing circuit 18 determines the temporal difference between the two pulses arising from the two axially arranged detectors. The temporal difference is proportional to the particle's velocity, which in turn is inversely related to the particle's size.

The timing circuit 18 also determines the temporal position of the particle along the beam path. The combination of the velocity and the temporal position allows the timing circuit 18 to determine when the particle passes an irradiation position within a time-of-flight mass spectrometer (TOFMS) 20. At that point, a dissociation laser 22 produces an intense light pulse directed at that point. The dissociation laser 22 ablates molecularly sized sub-particles from the already measured particle. Either the dissociation laser or a secondary laser ionizes the sub-particles into ionized sub-particles, for which the mass spectrometer 20 then analyzes the m/z ratio, that is, the ratio of the mass to the electronic charge of that particle. Assuming that the sub-particles are molecules, the m/z ratio provides in most cases a definitive determination of the chemical composition of the particle. Both the m/z ratio and the particle size are separately provided to a data acquisition unit 24 that can correlate the two sets of inputs. That is, the data acquisition unit 24 provides a spectrum of particles delineated both as to size and to m/z ratio of constituent atomically sized molecules which the laser irradiation desorbs from the macro particles.

The mass spectrometer described in the above patent application is in fact a unipolar spectrometer that allows the determination of either the positively charged state or the negatively charged state of the excited entrained atomically sized particles liberated by the dissociation laser. However, in a realistic polydisperse environment, both positively and negatively charged constituent molecules are present. Bipolar or dual ion spectrometers have been disclosed by Downey in U.S. Pat. No. 5,382,794.

The apparatus described above by Prather is in fact an experimental model that has been tested primarily in the laboratory. Its usefulness in a field environment has not been established. A field-usable instrument should be rugged, should not be prone to disalignment during transport, should be relatively compact and movable, should have readily available power, and should not consume excessive power.

SUMMARY OF THE INVENTION

The invention can be summarized as an analyzer for determining the size and chemical composition of particles in an aerosol.

Although the analyzer of the invention is achievable in a number of configurations, an acceptable configuration includes: (1) an aerosol interface including a nozzle and one or more skimmers, all differentially pumped, to produce a well defined beam of aerosol particles with the particle velocity inversely related to the particle size; (2) a dual-laser tracking system arranged along the particle beam for producing short electrical pulses as the particle passes the two locations at which the tracking laser beams strike the particle beam path; (3) a timing circuit providing both a velocity signal dependent upon the time difference between the two pulses and a trigger signal indicative of when the particle will pass a downstream ion source point; (4) a time-of-flight mass spectrometer, preferably bipolar, having an ion source region including the source point; (5) a laser aimed at the ion source point and triggered by the trigger signal; and (6) a data acquisition system for collecting data and capable of collating the mass/charge spectrum from the mass spectrometer with the particle size.

In a first aspect of the invention, the stages on which the nozzle and skimmers are mounted are telescopically movable with respect to each other and include keying to maintain the alignment between the stages.

In a second aspect of the invention, the nozzle is mounted on a tube which may be withdrawn from the system to allow maintenance and cleaning of the nozzle. Optionally, the bore in which the nozzle tube is inserted is selectively blocked by a ball valve having an opening through which the nozzle tube passes, thereby allowing continued vacuum pumping of the system during nozzle servicing.

In a third aspect of the invention, the dual-laser tracking system includes two detector modules insertable as units into the chamber wall. Each detector unit may include an ellipsoidal mirror, with one focal point positionable in the beam path and the other at the entrance to the photodetector, preferably a photomultiplier tube. The ellipsoidal mirror includes two pairs of orthogonally arranged holes, one pair to freely pass the particles along their path and the other pair to pass the unscattered beam from a probe light source.

In an fourth aspect of the invention, the light sources of the dual-laser tracking system are two diode lasers, each mounted in an angularly adjustable mount allowing the diode laser beam to be aligned to strike the particle beam. Preferably, the angularly adjustable mount includes a ball and socket joint.

In a fifth aspect of the invention, the dissociation laser is mounted directly on the side of the spectrometer vacuum housing, to provide increased rigidity.

In a sixth aspect of the invention, the vacuum housing of the mass spectrometer is rotatably supported on its two ends to allow easy servicing of the interior of the mass spectrometer.

In a seventh aspect of the invention, the bipolar time-of-flight mass spectrometer is generally of the coaxial type with two reflectrons, each comprising a stack of circular, apertured ring electrodes. The ion source region includes positively and negatively biased separation electrodes creating two beams of negatively and positively charged molecules, respectively. Two flight tubes arranged between the source region and the electrode stacks are biased at or near to the voltage of the respective extraction electrode.

In an eighth aspect of each the invention, each circular flight tube is supported within a rectangular vacuum wall by insulating mounts, preferably plastic. Circuitry and feedthroughs thereby can be easily mounted on the vacuum wall.

In a ninth aspect of the invention, a canister containing the stack of coaxial reflectron electrodes is supported on an end facing the ion source region by a rotatable joint, and on the other end by an externally displaceable mounting rod, preferably of plastic, to allow the coaxial electrodes to be angularly positioned relative to the path of the ions.

In a tenth aspect of the invention, the stack of ring electrodes is captured by recesses in three or more plastic rods, and the rods are captured in axial grooves in the cylindrical canister.

Other features and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 4 is a side cross-sectional view of the nozzle in the sizing section of the analyzer.

FIG. 5 is a graph depicting the relationship between particle size and particle velocity, as measured by the dual-beam laser tracking system.

FIG. 8 is an axial cross-sectional view of the laser probe unit.

DETAILED DESCRIPTION OF THE PREFERRED EMBODIMENT

Figure 1:
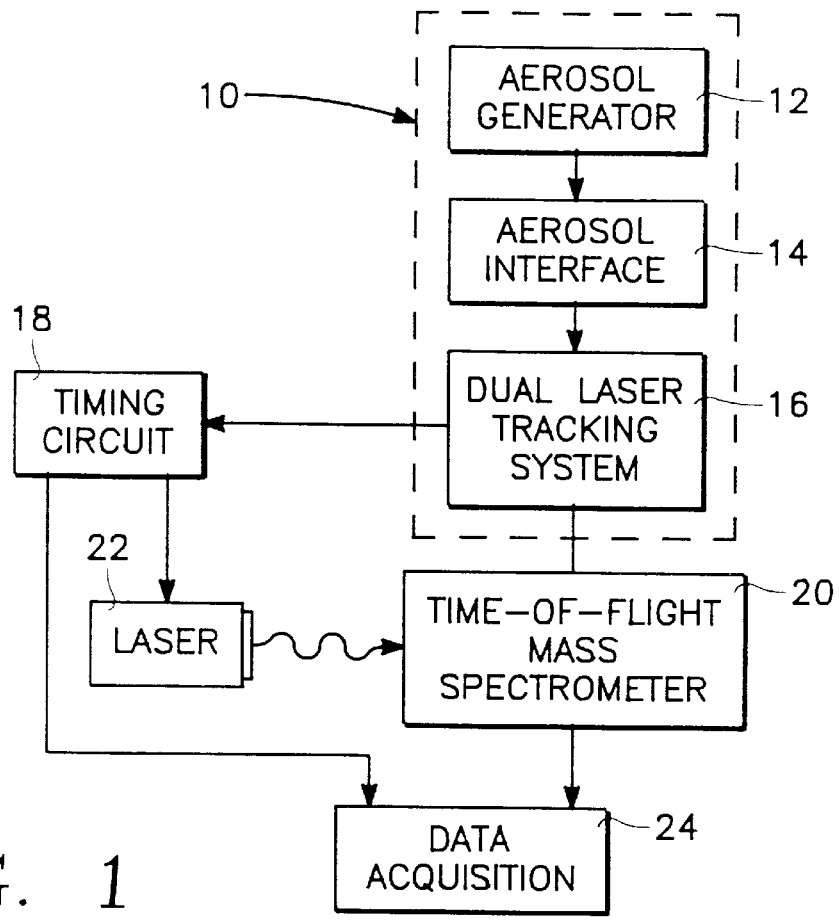
FIG. 1 is a schematic diagram of the operation of an analyzer for determining the size and chemical composition of an aerosol.
Figure 2:
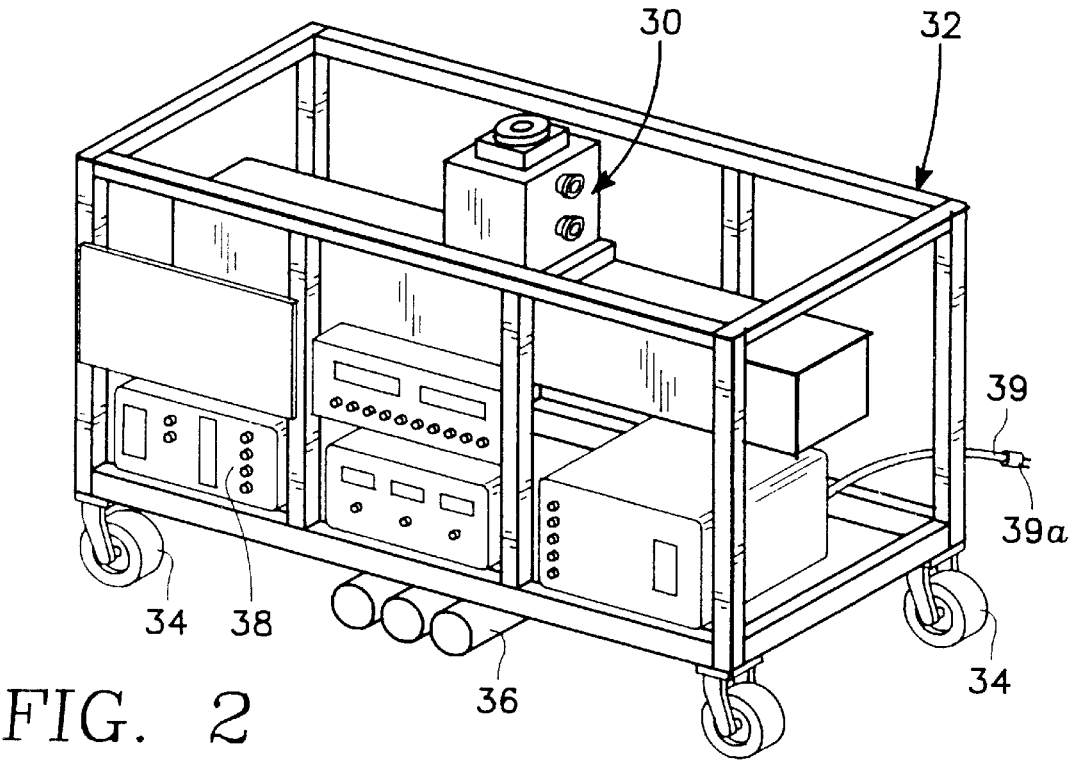
FIG. 2 is a pictorial illustration of a portable analyzer of the invention.

With reference now to the drawings, and particularly to FIG. 2, there is shown a portable analyzer 30 in accordance with the invention, which is transportable and sufficiently small and rugged to allow its dependable use in a field environment. Importantly, the analyzer is configured to remain in alignment, even with rough handling.

More particularly, the analyzer 30 is mounted on a cart 32 having three electronic equipment racks, and the cart is movably supported on pneumatic tires 34. In the preferred embodiment, the analyzer system is 183 cm×71 cm×152 cm, and it weighs about 225 kg, such that it can be wheeled through standard doorways and onto elevators. The analyzer system is small and sufficiently lightweight to be easily transported by helicopter, crane, or forklift, for use in less accessible locations, but more typically it can be transported by a truck having a lift gate. The cart 32, as illustrated, is configured like standard laboratory racks of extruded aluminum sections. The cart 32 mounts not only the analyzer 30, but also high-voltage power supplies, vacuum pumps, the data acquisition and display equipment, and other electronic equipment useful in calibrating, tuning, and operating the analyzer. A personal computer is mounted on the cart 32 for controlling the analyzer and for recording experimental data and includes a cart-mounted display and keyboard. Three mechanical roughing pumps 36 and heavy power supplies 38 are mounted low on the cart 32, for stability. Standard commercial power is supplied to the system by a power cord 39 with a socket 39a for a standard plug. In the initial prototype, separate power cords are connectable to commercial 120 VAC and 240 VAC power. However, the power supplies can be changed to accept other types of power, such as aboard a truck, ship or aircraft or in a mine. The power must be conditioned for kilovolt dc instrumentation associated with the mass spectrometer and with volt-level dc power for digital dc control equipment and laser power supplies. For dependable operation, the various power supplies should be interlocked to prevent accidents.

The analyzer configuration has been optimized for ruggedness and to minimize the need for field calibration and maintenance. The first model of the analyzer system was built and calibrated in the laboratory, depowered, transported 150 km by truck, and was collecting data ten minutes after unloading, without further calibration.

Figure 3:
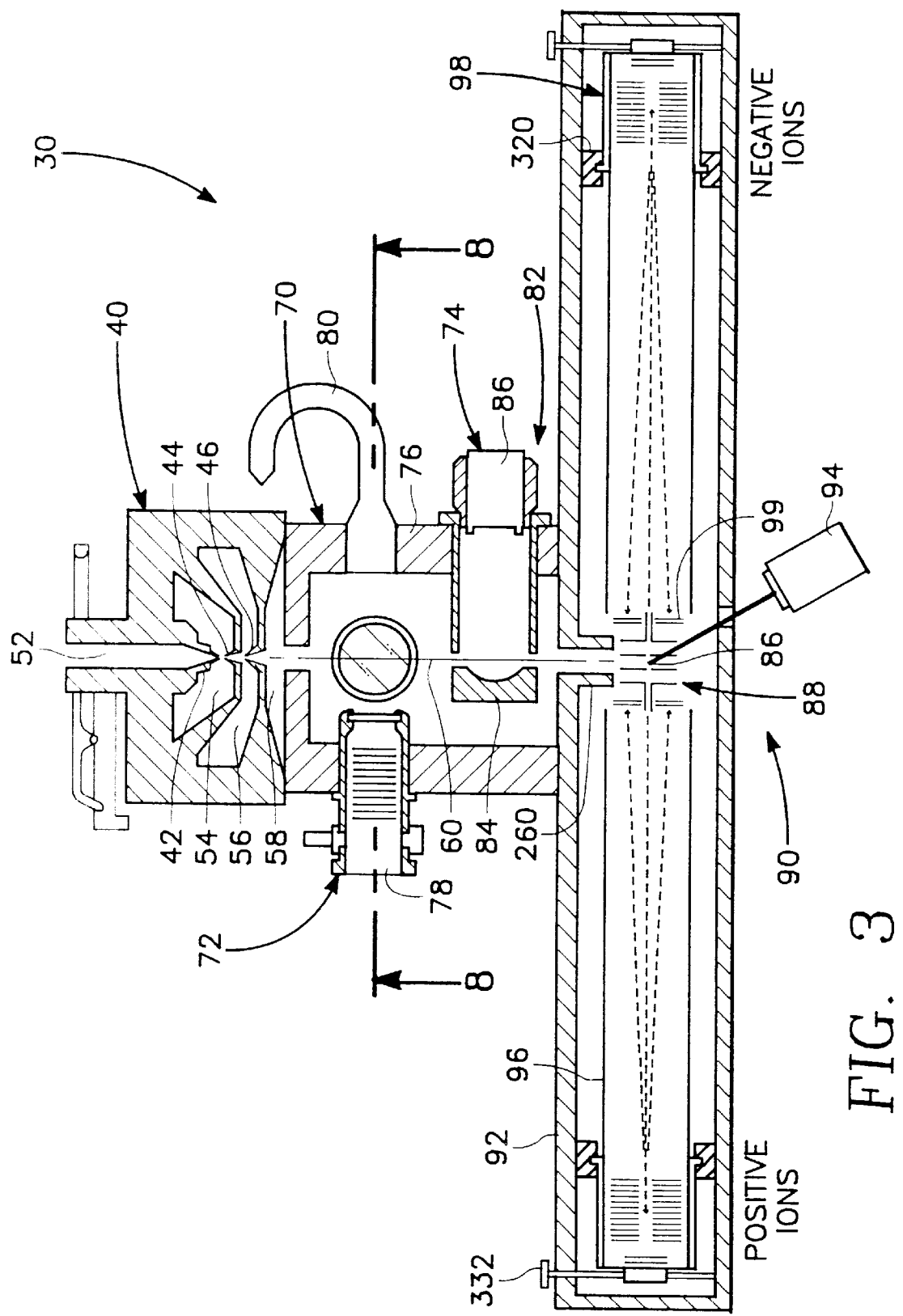
FIG. 3 is a side cross-sectional view of a principal portion of the analyzer of the invention.
Figures 4, 5, 8:
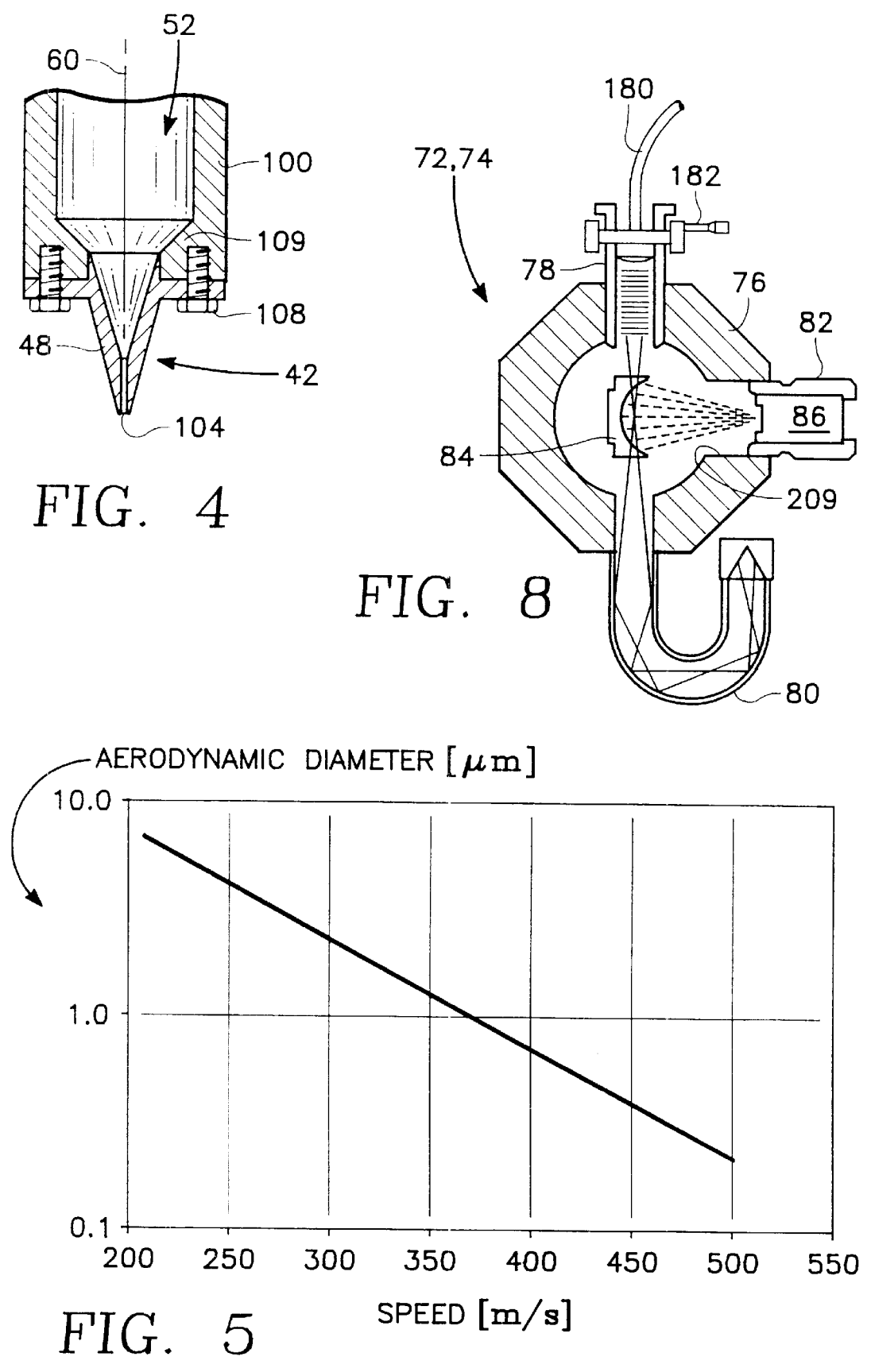

The principal parts of the analyzer are illustrated in the cross-sectional view of FIG. 3. An aerosol interface 40 includes a nozzle 42 and two skimmers 44, 46. An enlarged cross section of the nozzle 42 is shown in FIG. 4 as having a downstream-facing tip 48.

With reference again to FIG. 3, the nozzle 42 forms the top of a first chamber 54. The first skimmer 44 forms the bottom of the first chamber 54 and the top of a second chamber 56, while the second skimmer 46 forms the top of a third chamber 58, which is in free gaseous communication with the subsequent section of the analyzer.

The nozzle 42 and the first and second skimmers 44, 46 are arranged along, and define, a beam axis 60. The differential pressure across the nozzle accelerates the gas and any entrained particles to supersonic speed, and the resultant velocity of each particle is inversely related to the particle's aerodynamic size. A differential pressure is applied across each of the skimmers 44, 46, which pass the middle portion of the beam including most particles, but peel away most of the gas, which is then pumped out of the system.

After the aerosol has left the second skimmer 46, the particles previously suspended in the aerosol are traveling in a narrow beam along the beam axis at a high velocity of a few hundred meters per second. Two systems were calibrated using the dual-laser system to be described later to determine the speed of precisely sized nebulized polystyrene latex spheres suspended in a methanol/water solution. Although there were small differences between the systems, both generally followed the relationship between the aerodynamic diameter and particle speed given by the straight line 62 in the semi-logarithmic plot of FIG. 5, i.e., there is a negative exponential dependence of the size of the aerosol particle upon the particle velocity.

With reference again to FIG. 3, after the aerosol particle has passed through the aerosol interface 40, the particle enters a dual-laser tracking system 70, which principally includes two beam probes 72, 74 fixed to a chamber wall 76, downstream of the second skimmer 56. Each beam probe 72, 74 includes a light source 78 aimed at the particle beam 60, a light horn 80 for absorbing the unscattered portions of the light beam, and a light detector module 82 including a mirror 84 and a light detector 86. Preferably, the light detector 86 is a photomultiplier tube (PMT).

The dual-laser probe system 70 provides at least two time-related signals used in the operation of the analyzer, the time elapsed between the detection of the particle at the two beam probes 72, 74, and the time that the particle will arrive at a dissociation point 86, which is located at an ion source region 88 of a mass spectrometer 90.

A pulsed laser 94 is aimed at the dissociation point 86. The short intense pulse triggered by the dual-beam laser system 70 desorbs individual molecules from the detected aerosol particle just as it reaches the dissociation point. The intensity is sufficiently high to ionize a substantial fraction of the desorbed molecules. The mass spectrometer 90 includes separate ends of nearly the same design, which use the same ion source region 88 but which are biased to separately process positive and negative ions.

As shown in FIG. 3, the mass spectrometer 90 is a dual time-of-flight spectrometer, with two nearly symmetrical ends capable of processing positive and negative ions. The spectrometer is contained within a metal housing 92, and it has a common ion source region 88, but its two ends are biased separately negatively and positively. Each end operates as a coaxial reflectron-type mass spectrometer, in which the ions are accelerated in and near the ion source region 88 and then separated according to velocity in a field-free drift tube 96, after which they are reflected in a coaxial reflectron 98 in the opposite direction, generally along the same axis. An annular detector 99 positioned close to the source region 88 detects the reflected ions and provides a time spectrum of each of the particles, thus providing a mass-to-charge spectrum. Reflectrons are described generally by De Hoffman et al. in *Mass Spectrometry: Principles and Applications*, (John Wiley, Masson, 1996), pp. 59–66. They function to provide a region of nearly constant electric field to reflect the particles back toward the source. Their finite extent compensates for energy spread in the particle beam.

The discussion will now provide details of many of the elements described generally above.

The aerosol interface 40 is illustrated in more detail in FIG. 6, which shows the instrument in its operational mode, with nozzle 42 positioned close to the skimmers 44, 46. The nozzle is supported by a nozzle tube 100, and it includes an orifice 104. Three screws 108 hold nozzle to the bottom of an inwardly extending lip 109 of the nozzle tube 100, the interior of which forms the aerosol inlet port 52.

With reference again to FIG. 6, the aerosol inlet port 52 is maintained at essentially atmospheric pressure, while a mechanical pump connected to a vacuum port 110 maintains the pressure in the first chamber 54 on the downstream side of the nozzle 42 at about 2 Torr. This thus provides a flow rate of about 20 standard milliliters of aerosol gas per second into the analyzer. A vacuum flange 112 is welded to the top of the nozzle tube 100, to allow attachment of the inlet port 52 to environmentally controlled chambers that are to be tested. Note the generally low profile in the illustrated position. The vacuum flange 112 rests on a collar 113, and the nozzle tube 100 slides vertically within the collar 113, to allow its complete manual removal from the system. This facilitates nozzle servicing.

Although the described analyzer system is configured for monitoring ambient air at atmospheric pressure, it can be easily adapted to monitor a chamber at reduced pressure, e.g., a reactor for fabricating semiconductor integrated circuits. For somewhat reduced pressures, the analyzer can be modified by changes in the pressure applied across the stages. For very reduced pressures, different type of aerosol interfaces are required, such as disclosed by McMurry et al. in U.S. Pat. No. 5,270,542.

Both skimmers 44, 46 have orifice diameters of 0.5 mm. The orifice of the first skimmer 44 is located nominally 2 mm from the exit of the nozzle 42, and the two skimmers 44, 46 are nominally separated from each other by 2 mm. Two other mechanical vacuum pumps connected to two vacuum ports 114 maintain the second chamber 54 at a pressure of $5 \times 10^{-2}$ Torr. A turbomolecular pump evacuates the particle sizing area, which is in communication with the third chamber 58, via a passage 116, to a pressure of $5 \times 10^{-5}$ Torr. Two larger turbomolecular pumps, mounted on the spectrometer housing 92, maintain the mass spectrometer 90 at a pressure of $2 \times 10^{-7}$ Torr. The skimmers 44, 46 and the nozzle 42 thus isolate the mass spectrometer 90 from ambient pressure, while injecting the aerosol particles into the mass spectrometer 90.

The nozzle 42 and the nozzle tube 100 are detachably supported on a generally cylindrical first stage 120. In turn, the first skimmer 44 is mounted on a generally cylindrical second stage 122, and the second skimmer 46 is mounted on a generally cylindrical third stage 124. The third stage 124 is supported on a tubular wall 76 associated with the dual-laser tracking system 16. If desired, a third skimmer may be mounted on a support fixed to the tubular wall 76. The bottom of the nozzle tube 100 passes through a closely fitting Teflon collar 128 that provides more rigidity to the dependent nozzle 42 than does the slightly larger bore passing through the first stage 120. The three stages 120, 122, 124 are telescopically nested and can be moved axially with respect to each other and to the tubular wall 76 of the next section, while O-rings inserted in respective O-ring grooves 130, 132, 134 maintain a vacuum seal between the three stages. The upper two O-ring grooves 130, 132 are two-sided grooves disposed at the upper inner corners of the stages 122, 124. Their included O-rings serve not only to seal the downwardly descending cores, but also seal the next above stage. The placement of the O-ring grooves 130, 132 at the corners facilitates cleaning of the grooves and increases the allowed stroke of the stages 120, 124, 126 with respect to each other.

In operation, a set of bolts (not shown) fixes the stages 120, 122, 124 to the wall 76 and fixes the wall 76 to the planar vacuum wall 92 (FIG. 3) of the of the mass spectromer 90. However, the spacing between the stages 120, 122, 124 can be adjusted by inserting annular, disk-shaped shims between the stages. Such shims should include radially inner portions for sealing the O-rings in the grooves 130, 132. The shims allow adjustment of the spacings between the first and second stages 120, 122 and between the second and third stages 122, 124, thereby allowing the spacings between the nozzle 42 and the skimmers 44, 46 to be adjusted between about 2 mm and 9 mm, for linearizing the response of the sizing section. However, because of the close fit of the inner and outer cylindrical walls of the telescopically nested stages 120, 122, 124, the stages remain in alignment about the particle beam axis 60.

Figure 6:
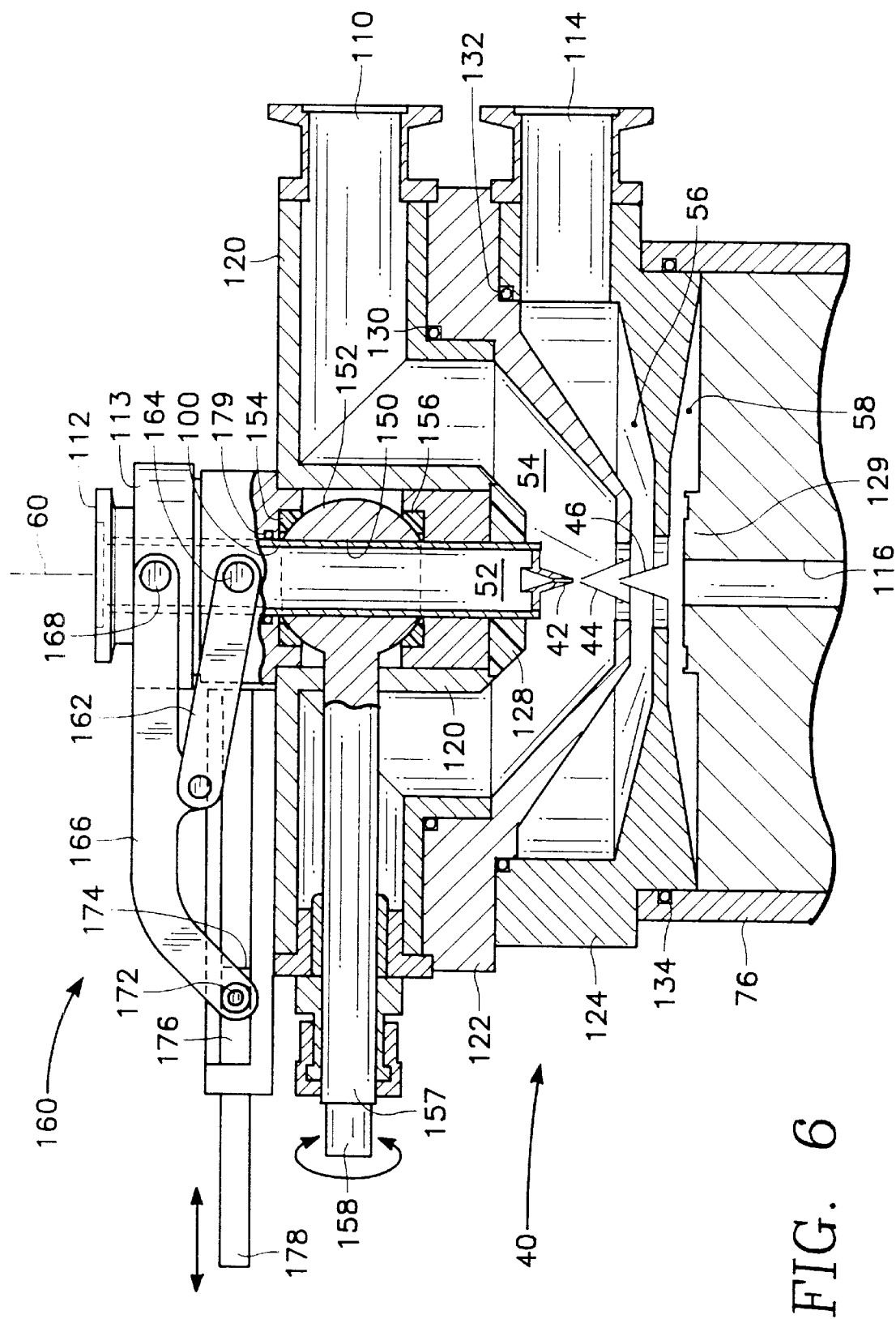
FIG. 6 is a side view, partially in cross section, of the aerosol interface positioned in an operable mode.

In the operational mode depicted in FIG. 6, the nozzle tube 100 with the nozzle 42 on its lower end passes vertically through a cylindrical hole 150 in a ball valve 152. This ball valve is sealed to the first stage 120 by two seals 154, 156. The ball valve is fixed to a rotatable shaft 157 having a handle 158 lying generally horizontally in the operational mode.

The vertically movable nozzle tube 100 is mechanically raisable by a linkage 160 having one link 162 pivotable about a pivot point 164 on the first stage. A second link 166, which is pivotably linked by a pin 167 to the first link 162, has one end pivotable about a pivot point 168 on the collar 113 through which the nozzle tube 100 passes and another end pivotable about a pivot point 172 on a slide 174 captured but horizontally movable in a channel 176 in the first stage 120. A handle 178 horizontally moves the slide 174, to thereby vertically move the nozzle tube 100 in the first stage 120 to the position shown in FIG. 7. The nozzle tube 100 and its end vacuum flange 112 are manually removable from the collar 170, to service the nozzle 42.

As shown in FIG. 6, the nozzle tube 100 is sealed to the first stage 120 by an O-ring positioned within an O-ring groove 179 in the first stage 120. The position of the O-ring groove 160 preferably is located sufficiently above the ball valve 152 (higher than the illustrated position) to allow the O-ring seal to remain effective even at a position where the nozzle tube 100 is raised sufficiently high for its attached nozzle 42 to clear the ball valve 152.

Figure 7:
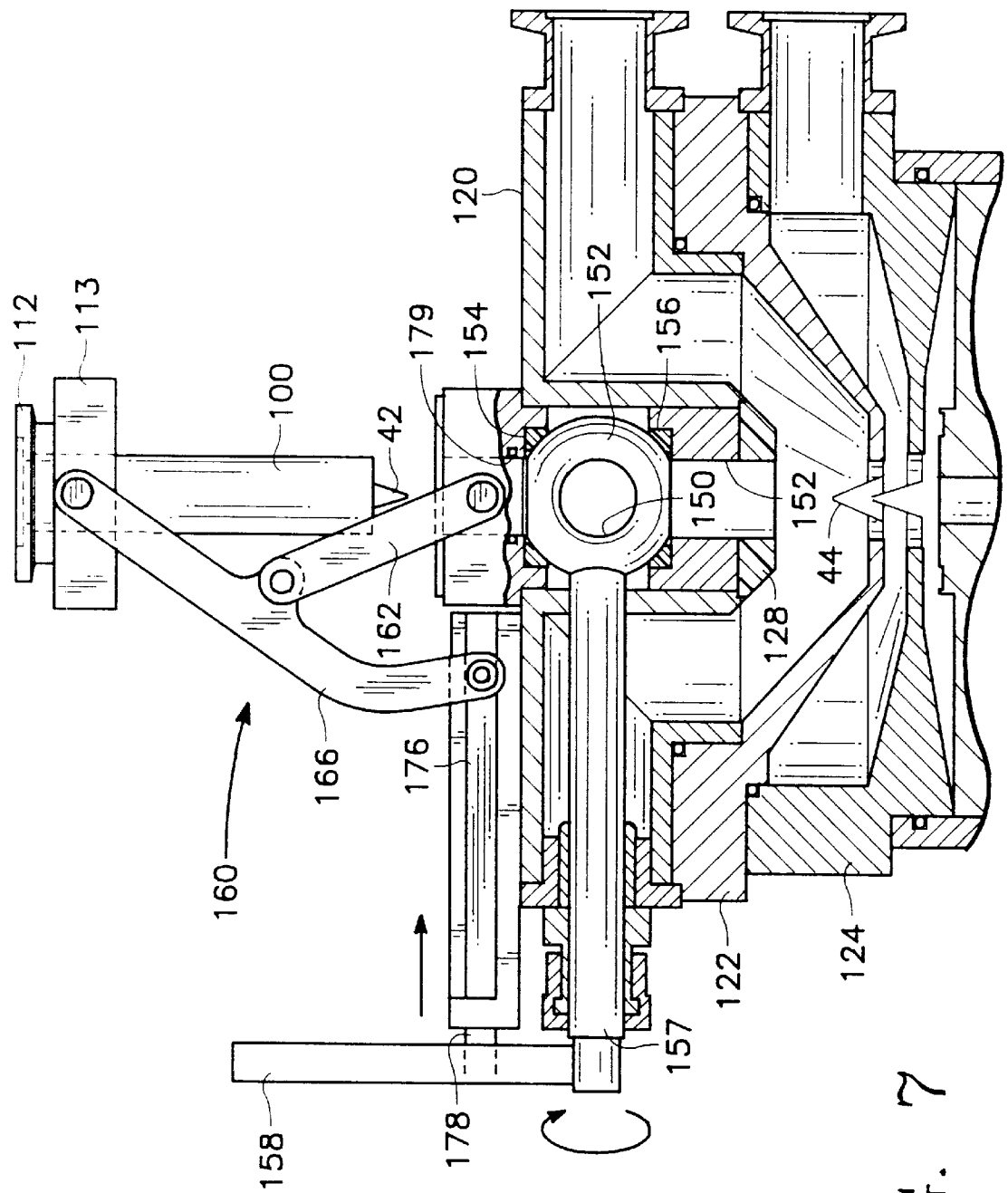
FIG. 7 is a side view, partially in cross section, of the aerosol interface of FIG. 6 positioned in a maintenance mode.

The nozzle 42 tends to clog during field usage, and it needs to be replaced and cleaned under difficult field conditions and often with limited field time available. Although the mechanical vacuum pumps can pump the slow leak through the nozzle 42 and skimmers 44, 46, they would fail if they attempted to continue pump with the nozzle bore exposed to atmospheric. However, if the vacuum pumps are turned off during nozzle servicing, an extensive pump down is required to return the analyzer, especially the mass spectrometer, to the required vacuum levels. The ball valve 152 is used to seal the analyzer during nozzle servicing. First, the slide handle 178 is pushed in to the point for the nozzle 42 to clear the ball valve 152. Then, as illustrated in FIG. 7, the ball shaft handle 158 is raised to the vertical position, to turn the ball valve 152 so that the ball hole 154 is horizontal or at least away from the seals 152, 154, thereby sealing the lower portions of the apparatus. The slide handle 178 is then pushed in further to raise the nozzle tube 100 and attached nozzle 42 completely out of the first stage 120. In this position, the nozzle 42 can be easily and quickly serviced while the vacuum system continues to maintain the interior of the analyzer at the usual vacuum levels. Thereby, the nozzle 42 can be quickly and easily serviced, and the system can be quickly returned to operation after servicing, important features in field operation.

The ball-joint handle 158 and the slider handle 178 are interlinked to prevent the delicate nozzle 42 from being lowered into the ball valve 152 while in its closed position. They are preferably further interlocked to prevent the nozzle tube 100 being raised above the O-ring seal 179 without the ball valve 152 having been rotated to its closed position.

The dual-laser tracking system 70, illustrated in the side cross-sectional view of FIG. 3, receives the aerosol particles injected from the aerosol interface 40. The tracking system 70 includes two identical optical beam probe units 72, 74, illustrated in axial cross section in FIG. 8. Note that the correct orientation of the light horn 80 is shown in FIG. 8. The two beam probe units 72, 74 differ in their being separated by a fixed space along the particle beam axis 60, 6 cm in the built version, and in their azimuthal orientations to the particle beam axis being offset by 90°. As previously described, each beam probe 72, 74 includes a laser beam source 78 irradiating a laser probe beam perpendicularly to the particle beam axis 60 and towards a light horn 80, which captures any unscattered radiation.

In one embodiment, a single continuous-wave argon ion laser has its beam split by an optical power splitter into two beams, and optical fibers 180 connect the outputs of the power splitter to the two laser beam sources 78. The optical fiber 180 is preferably a multi-mode fiber. An example of the argon ion laser is the Ohmichrome, Model 532. An example of the optical fiber power splitter for such a fiber is Model 2-107842-1, available from AMP. This arrangement both reduces the cost and simplifies the laser alignment of the analyzer 30 when the output end of the fiber is held in an XZ mechanical translator 182 affixed to the octagonal chamber wall 76.

Figure 9:
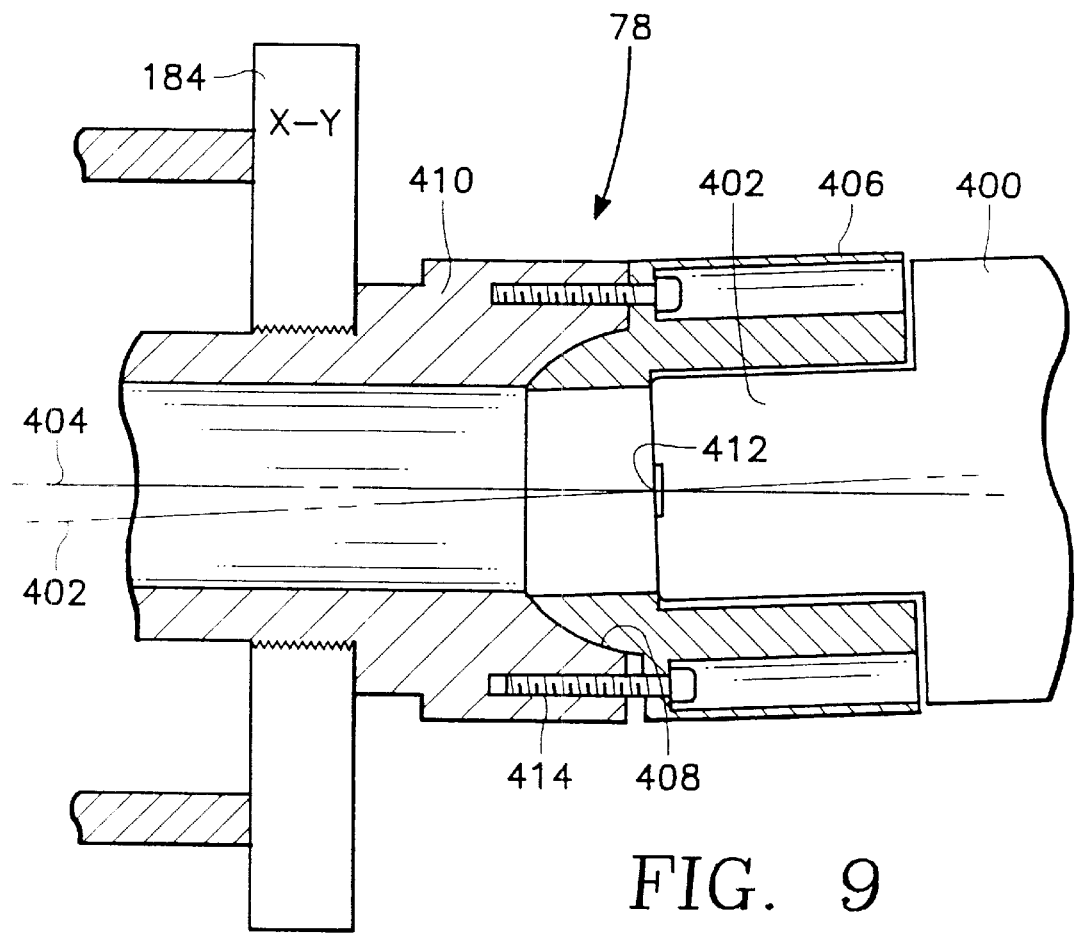
FIG. 9 is a cross-sectional view of an angularly adjustable mount for supporting the diode laser on the chamber wall.

An alternative preferred embodiment of each light beam source 78, illustrated in the cross-sectional view of FIG. 9, includes a separate diode laser 400 having a generally cylindrical housing 402 with a central axis 403. However, a diode laser can emit light along a beam with an axis 404 offset from the housing axis 403. To provide the necessary alignment to the very narrow particle beam 60, the diode housing 402 forms part of a joint housing 406 having a spherical or ball-and-socket joint 408, with a ball formed in the joint housing 406 and a socket formed in a light source mount 410. The center of the spherical joint 408 falls on the output facet 412 of the laser diode at which the two axes 403, 404 should intersect. Three or four screws 414 selectively tilt the joint housing 406 with included diode housing 402 with respect to the light source mount 410, In this manner, the diode beam axis 404 can be adjusted to coincide with a straight line to the particle path 60 with the intersection of the axes 403, 404 occurring generally at the output of the laser 400. The light source mount 410 is threaded into the X-Y translator 184 fixed to the chamber wall 76, to provide additional alignment control. The spherical joint 408 could be substituted by a cylindrical joint, which can be used in combination with X-Y translator 184 or the rotation of the diode housing within the joint housing 406. Such diode lasers preferably are commercially available GaAs lasers. In the tested system, each laser emits light at 532 nm, but other wavelengths, and even pairs of wavelengths, can be used. The diode laser is lighter and more rugged than the argon ion laser, and alignment is easier to maintain. Furthermore, it consumes much less power than does an argon ion laser.

Lenses and irises focus the two laser probe beams to 1 mm spots at the particle beam axis 60, and thus at an aerosol particle moving along the axis. A portion of the impinging radiation is, thereby, scattered toward the photomultiplier tube (PMT) 82. The use of laser probe light is not required and other types of light sources may be used, but a laser beam easily provides the required intensity and collimation.

Figure 10:
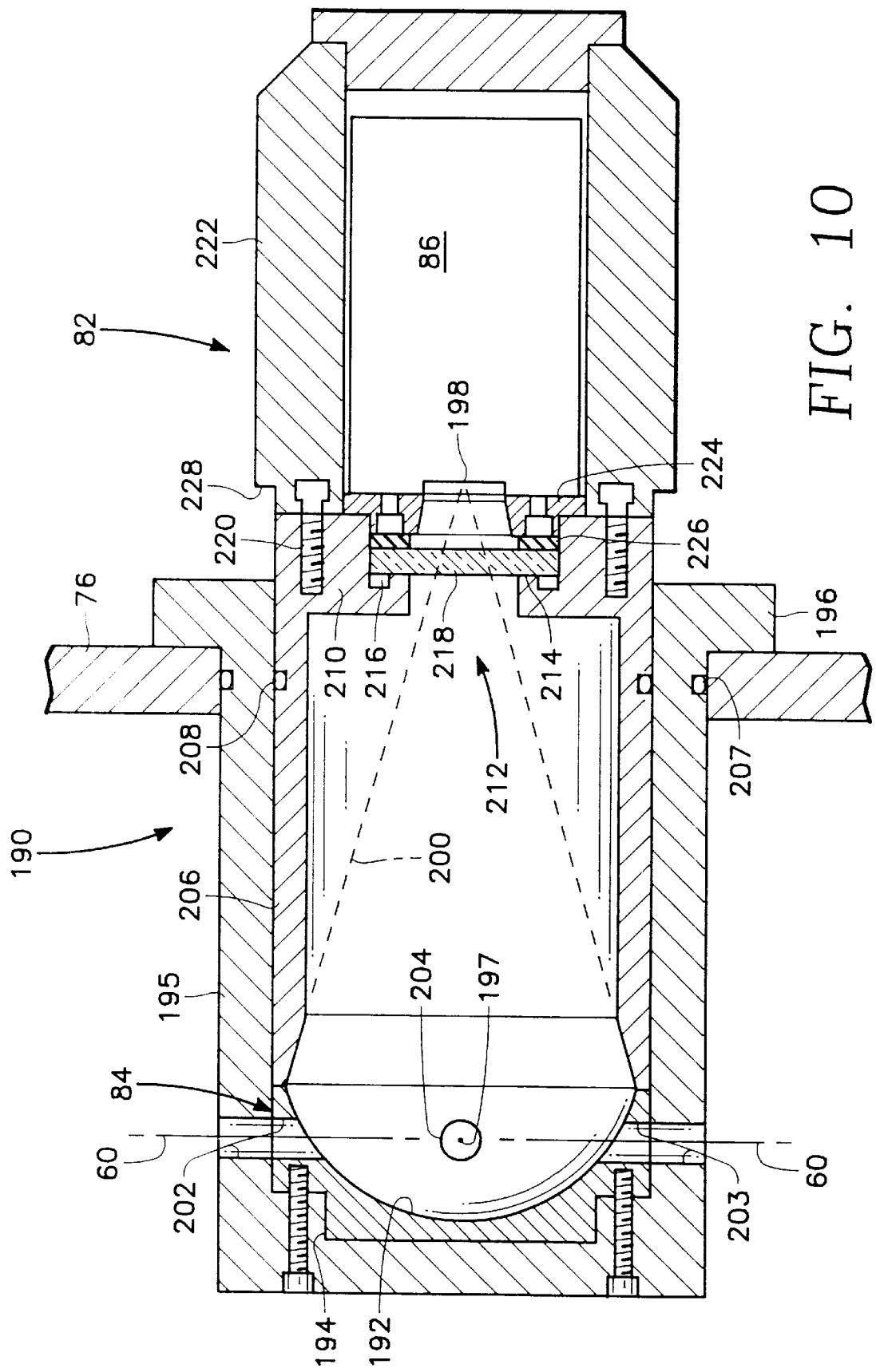
FIG. 10 is an enlarged axial cross-sectional view of the light detector module of the laser probe unit of FIG. 8.

As shown in FIG. 3, each beam probe 72, 74 includes the mirror 84 and the PMT 86, both incorporated into an optical detector module 120. This module is illustrated in more detail in FIG. 10. An ellipsoidal surface 192 is machined into a mirror body 194 and is coated with chrome, gold, or other highly reflective material. The mirror body 194 is threaded to a sleeve 195 having an outer annular rim 196 that registers the sleeve 195, and thus the mirror 84, to position one focal point 197 of the ellipsoid on the beam axis 60 and to position the other focal point 198 at the input to the PMT 86. Thereby, a large proportion of light scattered by particles at the first focal point 197 is collected by the PMT 82 from a converging beam 200. The use of an elliptical rather than a hyperbolic mirror increases the efficiency for a PMT positioned away from the particle beam.

The sleeve 195 is fastened by screws (not shown) to a flat external face of the chamber wall 76. The mirror body 194 is further formed with a vertical through hole 202, and the sleeve 195 is formed with a through hole 203, both holes arranged along the particle beam axis 60, for passing the aerosol particles. Similarly, the mirror body 194 and the sleeve 195 are formed with two horizontal through holes 204, for passing the unscattered laser beam from the light source 78 to the light horn 80

A tubular mirror spacer 206 is inserted from the outside of the mounted sleeve 195 and is mechanically biased to abut against the mirror mount 194. O-rings inserted into O-ring grooves 207, 208 in the sleeve 195 and the mirror spacer 206, respectively, allow the entire light detector module 190 to be sealably inserted into a circular hole 209 (FIG. 8) formed in a face of the octagonal chamber wall 76.

The outside lateral end of the mirror spacer 206 includes an annular lip 210 surrounding a central aperture 212 sized to receive the converging beam 200 from the ellipsoidal mirror 84. The back of the mirror mount lip 210 is formed with a circular recess having a planar annular surface 214 with an included O-ring groove 216. A window 218 that is transparent to the light scattered from the probe beam is positioned in the recess and presses the O-ring into its groove 216, thereby sealing the dual-laser chamber 76. Screws 220 fix a PMT mount 222 to the mirror spacer mount 206. A collar 224 is attached by screws (not shown), to the PMT 82 between the PMT mount 222 and a resilient annular pad 226 pressed against the back of the window 218. The PMT mount 222 includes a shoulder 228. The optical detector unit 190 is held to the chamber wall by the vacuum within the chamber although additional fasteners may be used to keep the elements in place when the vacuum is released. The photomultiplier tube 86, which is mounted on the PMT mount 222, may be a commercial available unit such as Model H55783, from Hamamatsu of Japan.

The optical detector unit 190 may be easily removed from the chamber wall 76, for cleaning and maintenance. The beam probe unit 72, 74 has demonstrated its ability to detect particles as small as 0.2:m.

Figure 11:
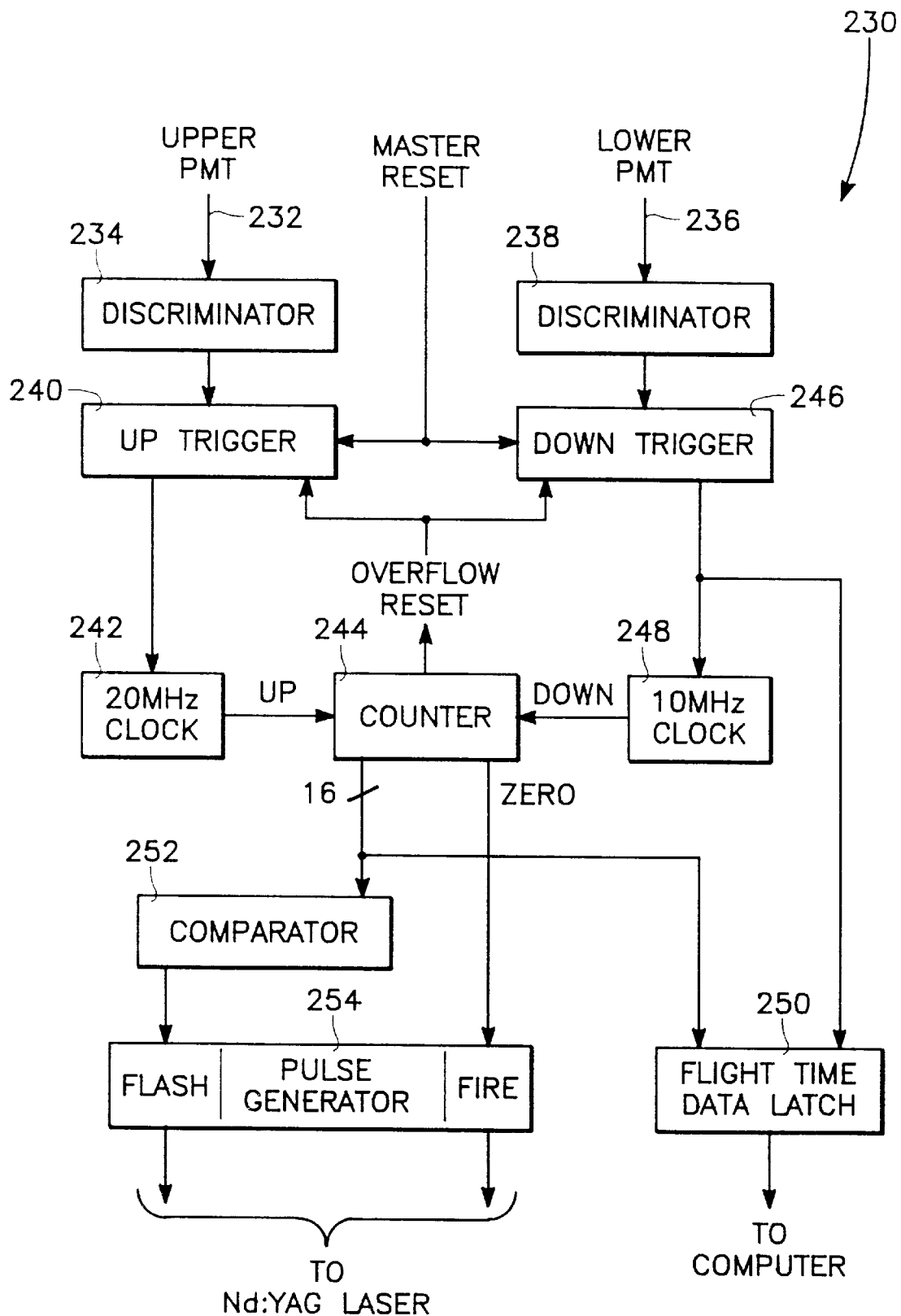
FIG. 11 is a block diagram of a timing circuit that processes the pulsed output signals of the photodetectors.

The two PMTs 86 in the dual-laser tracking system 70 provide two electrical pulse signals indicative of the time required for a single particle to traverse two separated points along the beam axis 60. A timing circuit 230, whose internal function is illustrated in the circuit diagram of FIG. 11, converts these two pulse signals into electrical signals used in other parts of the analyzer. The PMT 86 from the upper beam probe 72 provides an analog signal on line 232 to a pulse discriminator 234, which converts the pulse to a well defined TTL pulse. Similarly, the PMT 86 from the lower probe 74 provides an analog signal on line 236 to another such pulse discriminator 238. The pulse from the upper PMT initiates a count-up trigger 240, to start a 20 MHz clock 242 connected to the UP input terminal of a 16-bit digital counter 244. The count-up trigger 240, once initiated, locks out any other TTL pulses until it has been reset either by an overflow reset from the counter 240 corresponding to 800:s, or by a master reset from the computer controlling the operation. The lock out prevents a closely following particle from reinitiating the counter 244 prior to the detection of the particle at the second position.

The signal from the lower PMT 86 initiates a count-down trigger 246, which triggers a 10 MHz clock 248 connected to the DOWN input terminal of the digital counter 244. The difference in count rate corresponds to the 1:2 ratio between the separation of the two beam probe unit 72, 74 and the separation between the lower beam probe unit 74 and the center of the source region of the mass spectrometer 90. A relatively long post-detection drift is required to provide sufficient time to fire the Nd:YAG dissociation laser 94, which must be flashed 200±5:s before it is fired. The count-down trigger 246 at the same time sends a hold signal to a data latch 250 for the flight time detected between the two beam probe units 74, 76, i.e., the count in the counter 244 at the time of the signal from the lower beam probe unit 74. This value is provided to the data acquisition unit, as indicative of the speed and thus the aerodymanic size of the aerosol particle.

The 16-bit output of the counter 244 is supplied to a comparator 252, for comparison with a value indicative of +200:s according to the 10 MHz clock 248. When the count down reaches this value, a dual pulse generator 254, being properly enabled for the count down, pulses the flashtube of the Nd:YAG laser 94. When the count down reaches zero, the ZERO output of the counter 254 is supplied to the pulse generator 148, which fires the Nd:YAG laser 94. After the laser has fired, the computer reads the flight time data latch 250, acquires the two mass spectra from the mass spectrometer detectors 99, and sends a master reset signal to the triggers 240, 246, to prepare the timing circuit 230 for the next particle.

It is possible that a faster second particle will arrive at the second beam probe 74 before a slower first particle, previously detected by the first beam probe 72. If this occurs, the incorrect speed will be calculated so that the Nd:YAG laser 86 will fire when no particle is present at the dissociation point 86 in the mass spectrometer 90. In this situation, the mass spectrometer 90 should fail to produce a signal.

It is, of course understood the actual electronic circuitry may be implemented in other ways, including software. The circuitry incorporates design features well known in instrumentation control.

Figure 12:
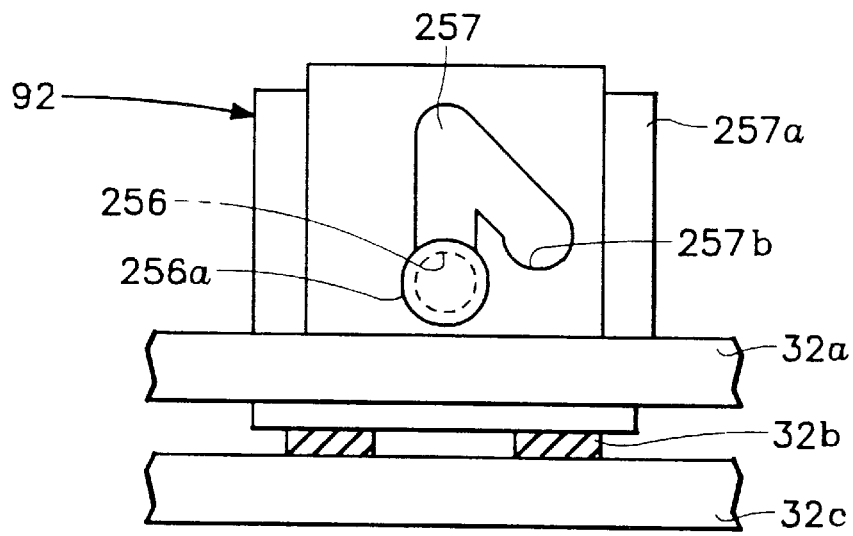
FIG. 12 is an end view of the spectrometer mount.
Figure 17:
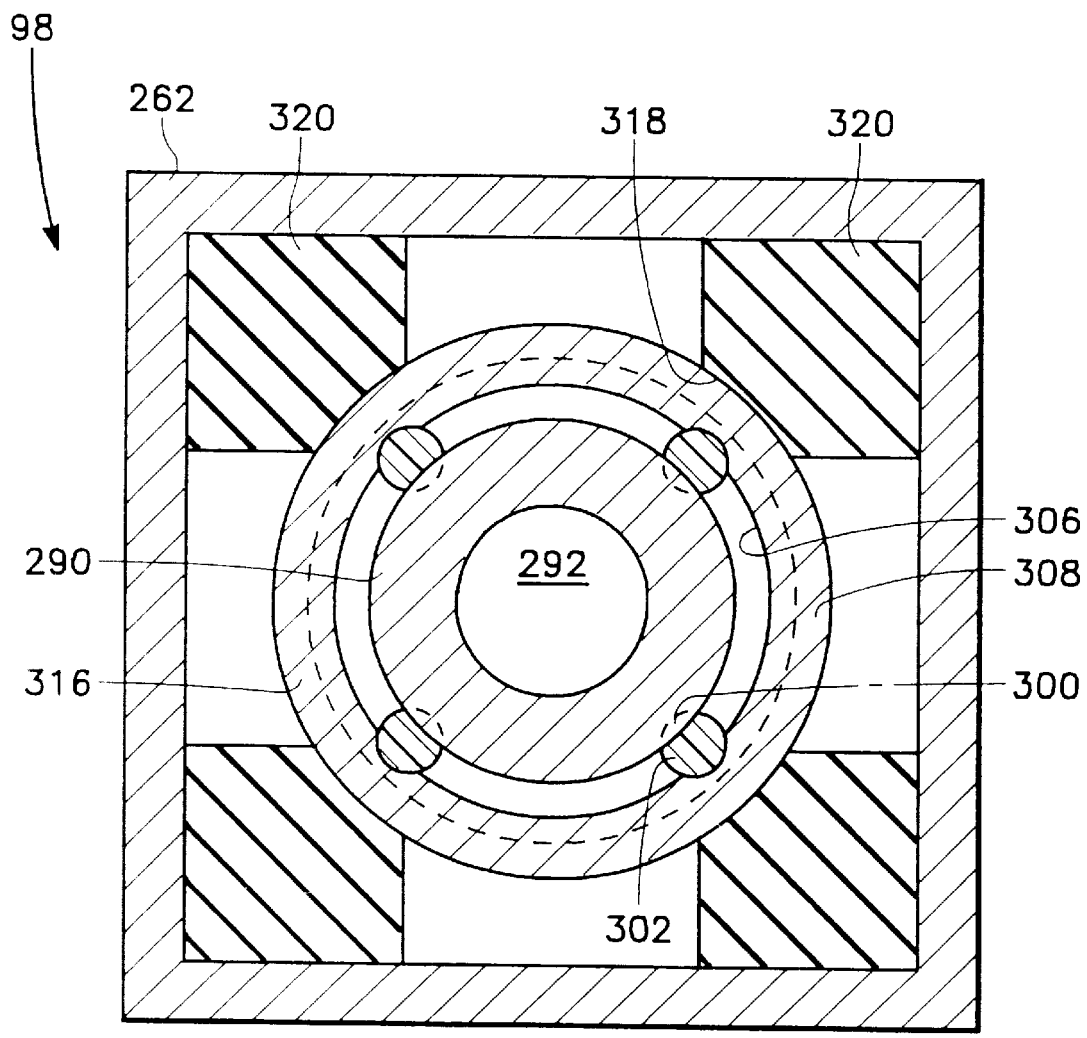
FIG. 17 is an axial cross-sectional view of the reflectron including one of the disk electrodes.

As illustrated in FIG. 3, the aerosol particle passing along the particle beam axis 60, after having its speed and time position determined by the dual-laser tracking system 70, enters the mass spectrometer 90. The mass spectrometer 90 is principally contained within the square housing 92. The dual-laser tracking system 70 and the aerosol interface 40 are mounted on the top side of the housing 92. The two ends of the housing 92 include shafts 256, as illustrated in the axial and view of FIG. 12, which are capable of supporting the housing 92 and attached elements. Each shaft 256 is inserted through a guide channel 257 in the shape of an inverted J formed in a guide plate 257 a fixed to a cross strut 32a of the cart 32. A retainer 256a, fixed to the end of the shaft 256, retains the shaft 256 within the guide channel 257, but allows the shaft 256 and attached housing to rotate within the guide channel 257.

During operation, the housing shafts 256 are located near the bottom of the guide channel 257, in the illustrated position, but they do not touch the bottoms. Instead, the housing 92 is elastically fixed through elastic supports 32b to another cross strut 32c of the cart 32, to suppress local vibrations. For servicing, the housing 92 is raised so that the shafts 256 travel upward in the guide channel 257 and then is set in a bottom circular pocket 257b. In this position, the housing 92 can be pivoted free of the supporting strut 32c, to thereby expose its bottom side, which includes a removable panel. In this position, the panel can be easily removed and the interior elements can be easily serviced without removing the mass spectrometer 90 from the cart 32.

The aerosol particle, after having its speed and time position determined by the dual-laser tracking system 70, enters the ion source region 88 of the mass spectrometer 90 through a tunnel 260 that restricts the gas flow between the tracking system 70 and the mass spectrometer 84. Thereby, the mass spectrometer 84 can be maintained at a very low pressure. The tunnel 260 may be 3 cm long and 0.3 cm in diameter.

Figure 13:
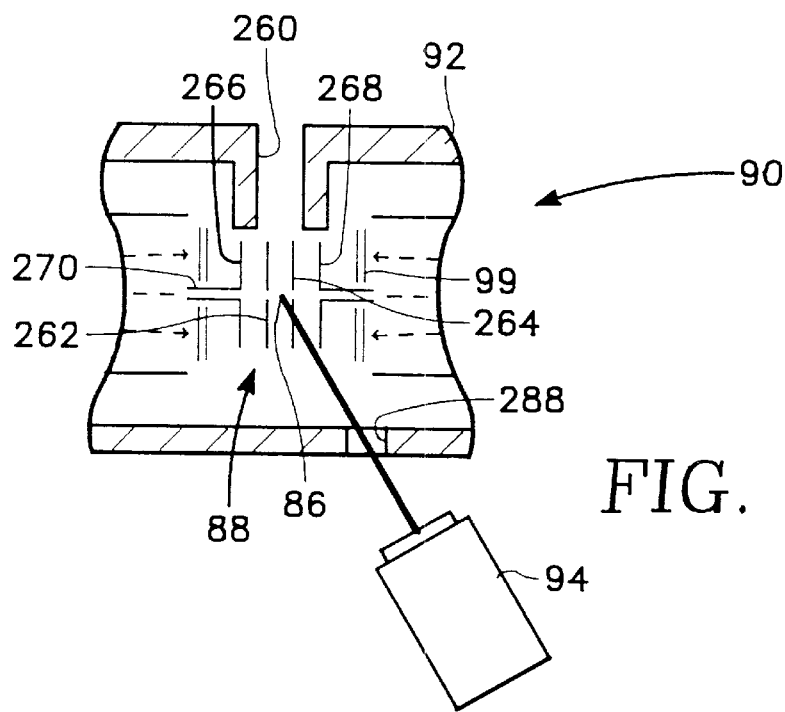
FIG. 13 in a side cross-sectional view of the ion source region of the mass spectrometer of FIG. 3.

As illustrated in FIG. 13, the particle beam 60 and the dissociation point 86 are located between two oppositely biased primary source electrodes 262, 264, with central apertures in the primary source electrodes defining ion paths within the mass spectrometer 90. Secondary source electrodes 266, 268, are located outside the primary source electrodes 262, 264, to further increase the bias applied to the two ion beams. Each secondary source electrode 266, 268 includes a central aperture and an electrically connected metal tube 270 penetrating through a central aperture in the particle detector 99. The particle detector 99 typically is composed of several highly biased layers, and the tube 270 protects the outgoing ions from the detector fields. When the mass spectrometer 90 is operated in the dual-ion mode, typical bias voltages are −4700 V and +1700 V applied to the primary source electrodes 262, 264, respectively, and −7800 V and +7800 V applied to the secondary source electrodes 266, 268, respectively, as well as to the corresponding adjacent flight tube 96. Electrons generated by the laser 94 in the source region 88 are attracted to the positive ion side. Because of their very light mass, they are detected within the first microsecond.

The combination of a sizing section and a mass spectrometer places extreme requirements upon the alignment between the two sections. Minute variations in the location of the particle beam 60 and in the placement of the dual-laser beam tracking station 70 renders it impossible for the mass spectrometer 90 and its dissociation laser 94 to produce a mass spectrum for the aerosol particle. Consequently, the two sections must be precisely aligned, and the alignment must be maintained during the transport of the portable analyzer. Further, the optical alignment for the dissociation laser 94 is critical.

Figure 14:
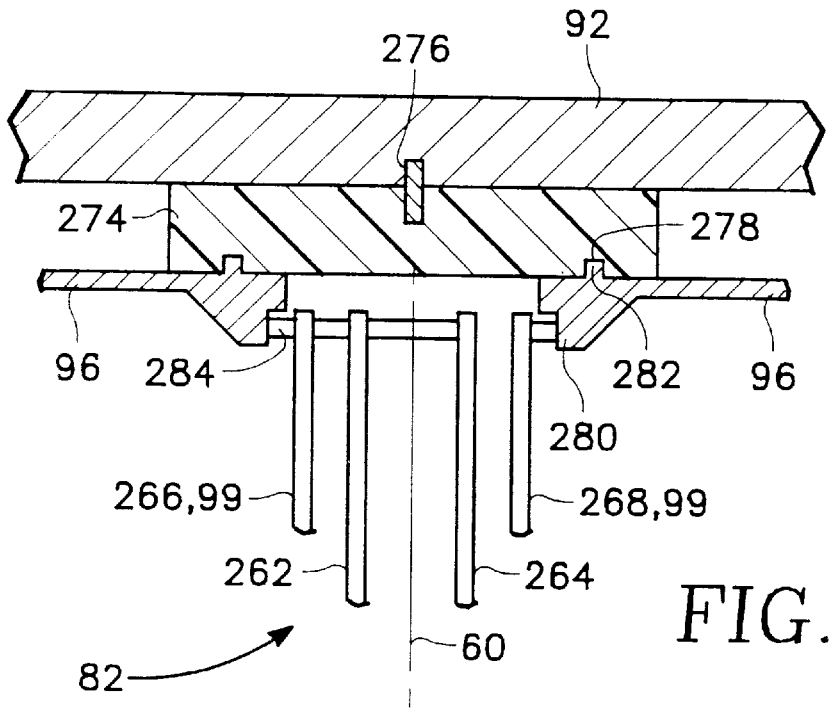
FIG. 14 is a cross-sectional view of the structure adjacent the ion source region for supporting the electrodes and the flight tube.

One technique for aligning the particle beam 60 with the mass spectrometer 90 is illustrated in FIG. 14, which is a diagonal cross-sectional view of the central part of the mass spectrometer. Four plastic insulating central mounts 274 are fixed by screws (not shown) to the corners of the mass spectrometer housing 92, in the area of the ion source region 88. Each of the central mounts 274 is precisely positioned with respect to the particle beam axis 60 by alignment pins 276 extending radially into the spectrometer housing 92. The four central mounts 274 include two inner annular grooves 278. Each flight tube 96 includes a central inner rim 280 including an outer circumferential band 282, which closely fits into the grooves 278 of the central mounts 274, thereby precisely positioning the flight tubes 96 with respect to the alignment pins 276 and the particle beam axis 60.

On the left-side central inner rim 280 of the flight tube 96 are mounted the combination of the positive second electrode 266 and the associated particle detector 99, the positive first electrode 262 and the negative first electrode 264, all separated by electrically insulating standoffs 284. Similarly, the combination of the negative second electrode 268 and its associated particle detector 99 are separated from the negative flight tube 96 by its insulating standoff. The asymmetry of standoffs allows the positive-ion spectrometer to be operated without the negative-ion spectrometer.

The ruggedness of the analyzer is enhanced by mounting the dissociation laser 94 upon the spectrometer housing 92. As illustrated in the pictorial view of FIG. 3C, the dissociation laser 94 is mounted in a housing 285 that is fixed to the spectrometer housing 92 by screws or perhaps welded thereto. The laser beam, propagating parallel to the axis of the spectrometer housing 92 exits the housing through a window 286, and a series of mirrors 287 direct the laser beam through a vacuum-sealed window 288 to the dissociation point 86 in the ion source region 88 of the mass spectrometer 90. One or more of the mirrors may be mounted on mechanical stages, to allow the laser 94 to be aligned with the dissociation point 86. A cover (not shown) protects the mirror 287 and the windows 286, 288.

The electrodes 262, 264, 266, 268 extract positively and negatively charged ions in opposite directions, at energies determined by the voltages applied to the electrodes. The ions then enter the essentially field-free region of the two flight tubes 96, illustrated in FIG. 3, with their respective corresponding potentials equal to the respective second electrodes 266, 268 on the flight-tube side of the detectors 99. The time of flight in the flight tube 96 is inversely proportional to the particle's speed, which is inversely proportional to the ion's mass. In the fabricated system, the flight tubes 96 are 50 cm long, and they prove a resolution of 600 at an m/z ratio of 165.

Figure 16:
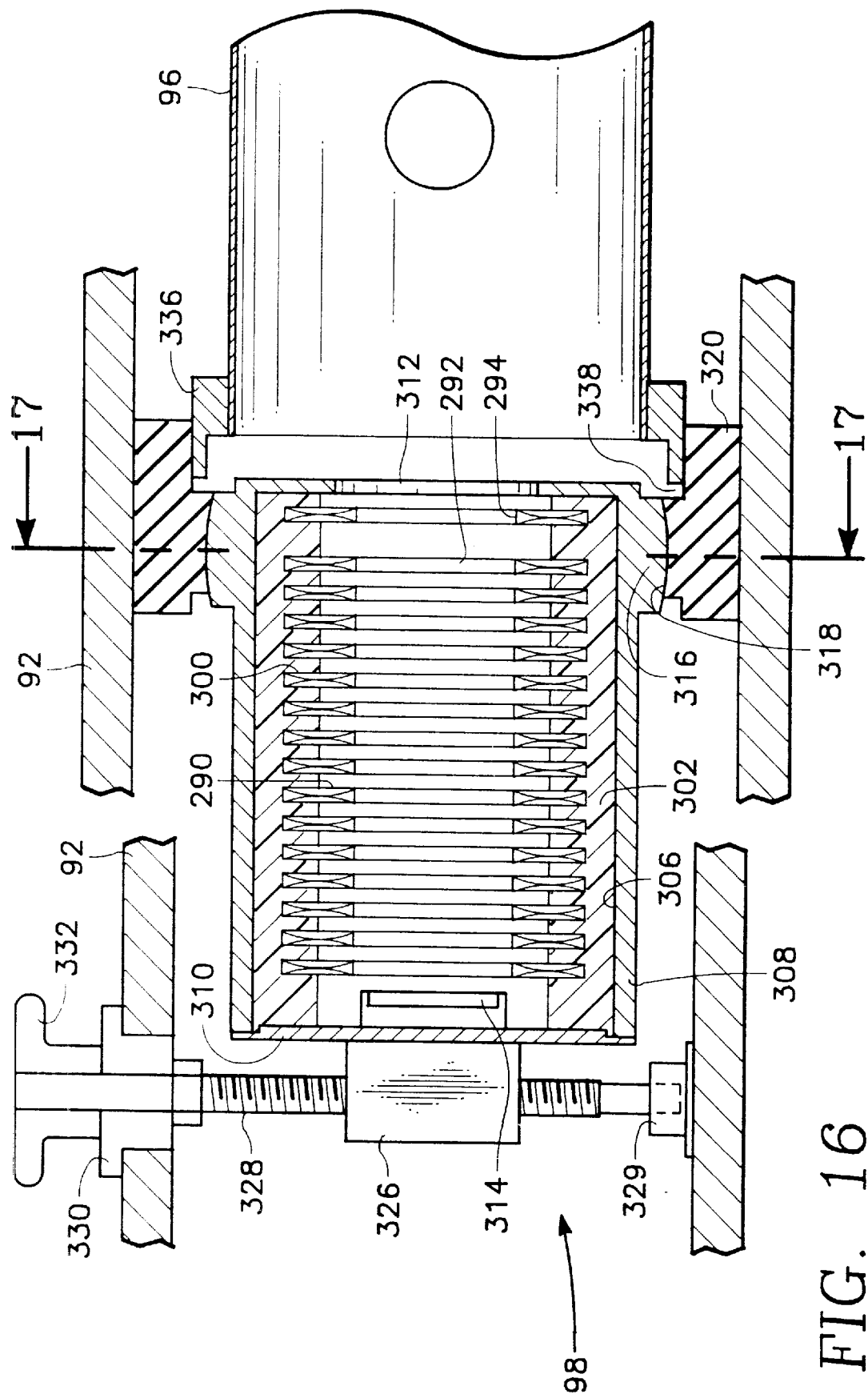
FIG. 16 is a side cross-sectional view of the reflectron and its supporting structure.

After traversing the flight tube 96, the ion enters into the reflectron 98 and is reflected back to its particle detector 99. Each reflectron 98, as illustrated in FIG. 16, includes 21 ring electrodes 290 of 306 stainless steel. Each ring electrode has a general disk shape, with a central aperture 292 through which the ions pass, generally along an axial path. A drift electrode 294 of the same shape is positioned adjacent to the drift tube 96, and it has the same potential so as to reduce the electric field in the drift region. The potentials of the ring electrodes 290 are linearly graded, so as to produce a constant axial electric field between them and to act a gradual brake on the incoming ions. The spacings of the ring electrodes 290 are constant, but the spacing between the front ring electrode 290 and the drift electrode 294 provides a configuration in which the front reflectron voltage is ⅔ of the flight tube voltage. Typical biasing voltages are −4458 V for the front ring electrode and +900 V for the back ring electrode for the positive-ion reflectron, and +1200 V for the front ring electrode and −4525 V for the back ring electrode 290 in the negative-ion reflectron. The asymmetric biasing voltages arise from a significantly different designs for the floating circuits associated with the particle detectors 99 for positive and negative ions and required by the millivolt signals induced on detectors 99 biased at thousands of volts.

It should be noted that FIG. 16 shows the mass spectrometer 90 to include two portions along the axial direction, which are offset by 45° in the azimuthal direction. This is evident from the depicted offset of the square spectrometer housing 92, i.e., the left portion of the view represents a cross section across the perpendicular of the square while the right portion represents a cross section across the diagonal.

The reflectron 98 incorporates has several features promoting its ruggedness and ease of alignment.

The periphery of each ring electrode 290 is closely received within a separate recess 300 of four plastic rods 302. These rods 302 are closely received within separate partial circular grooves 304 that extend axially along an inner wall 306 of a cylindrical metal cannister 308. The rods 302 are axially fixed by screws (not shown) penetrating a back wall 310 that is, in turn, fixed by screws (not shown) to the cylindrical side walls 308 of the cannister. The plastic provides sufficient elasticity to mechanically bias the ring electrodes 290 from the encircling cannister 308. Further, the plastic composition of the rods 302 electrically insulates the rods 302 from each other and from the cannister 308, which is maintained at the potential of the associated flight tube 96. A preferred plastic composition is Kel-F, available from DuPont. Kel-F is considered easier to machine and more resistant to cracking than ceramics. Although four rods 302 are illustrated, any number of three or more can be used. The front of the cannister 306 includes a central aperture 312 somewhat larger than the central apertures 292 of the ring electrodes 290. The back of the cannister 208 includes a detector mount 314 for a linear detector positioned at the end of the ion path. This detector can be used as a backup to the primary detector, for diagnostic purposes, or to determine neutral losses.

The ring electrodes 290 are connected in series by 10MS vacuum-compatible resistors. Each resistor has its two ends soldered with clips, and the clips are attached between neighboring ring electrodes 290 as they are being assembled into the cannister 308. Voltage supply wires are clipped to the front and back ring electrodes 290, and these wires exit the interior of the cannister 308 via holes, to feedthroughs in the planar chamber wall 92.

The structure of the reflectron does not include any grids, which are prone to breakage, and the structure of the recessed rods maintains the electrodes in alignment, with little chance for breakage. Nonetheless, the reflectron can be easily disassembled for maintenance in the field.

The operation of the reflectron requires the ions beam to diverge or to be deflected after reflection so that the ions are collected by the annular detector 99 positioned around the incoming ion beam. In some cases, the reflection can be so symmetric that the reflected ions travel back through the detector aperture. To preclude this, it is desirable to slightly cock the reflectron assembly with respect to the incoming beam, to destroy the symmetry and separate the incident and reflected beams.

To achieve this cokcing, the cannister 308 and associated ring electrodes 290 are rotatably mounted on a partial spherical joint, as shown in FIG. 16. The spherical joint includes an integral ring boss 316 extending completely around the outer circumference of the cannister 308, near its front. A surface 318 of the ring boss 316 also has toroidal radius, i.e., a spherical shape, centered along the central axis of the cannister 308, close to the frontmost ring electrode 290. The ring boss 316 acts as a partial ball of a ball-and-socket joint. The socket is segmented into four plastic spherical mounts 320, positioned in and threaded to the comers of the square chamber wall 92. Each mount 320 has a spherical surface conforming to that of the boss ring 316. The spherical mounts 320 are preferably made of Kel-F, provide easy sliding.

The back wall 310 of the cannister 308 is fixed to a nut box 326 having two orthogonally arranged threaded holes for screws 328 (only one of which is illustrated). Each screw is supported on one side by a bearing 329 fixed to one side of the chamber wall 92 and on the other side by a rotatable sealed joint 330 passing through the opposed side of the wall 262 to a handle 332. Turning the handle 332 pivots the cannister 308 and its ring electrodes 290 about a pivot point near the front of the reflectron 98. The two orthogonally arranged mechanisms allow full angular adjustment of the reflectron 98 from outside the vacuum housing 92. Preferably, the nut box 326 and the screws 328 are made of the Kel-F plastic, to electrically isolate the cannister 308 from the chamber wall 262.

The flight tube 96, likewise, is supported by the spherical mounts 320. A stainless steel collar 336 is welded to the flight tube 96, and it is slidably mounted to the four plastic spherical mounts 320. Thereby, the flight tube 96 is supported between the spherical supports 320 and the central mounts 274 (FIG. 14) near the ion source region 88, with an axial gap 338 formed between the flight tube collar 336 and the spherical mounts 320, to allow for thermal expansion of the flight tube 96. The flight tube 96 is electrically isolated from the chamber wall 92 by the plastic spherical supports 320.

Figure 15:
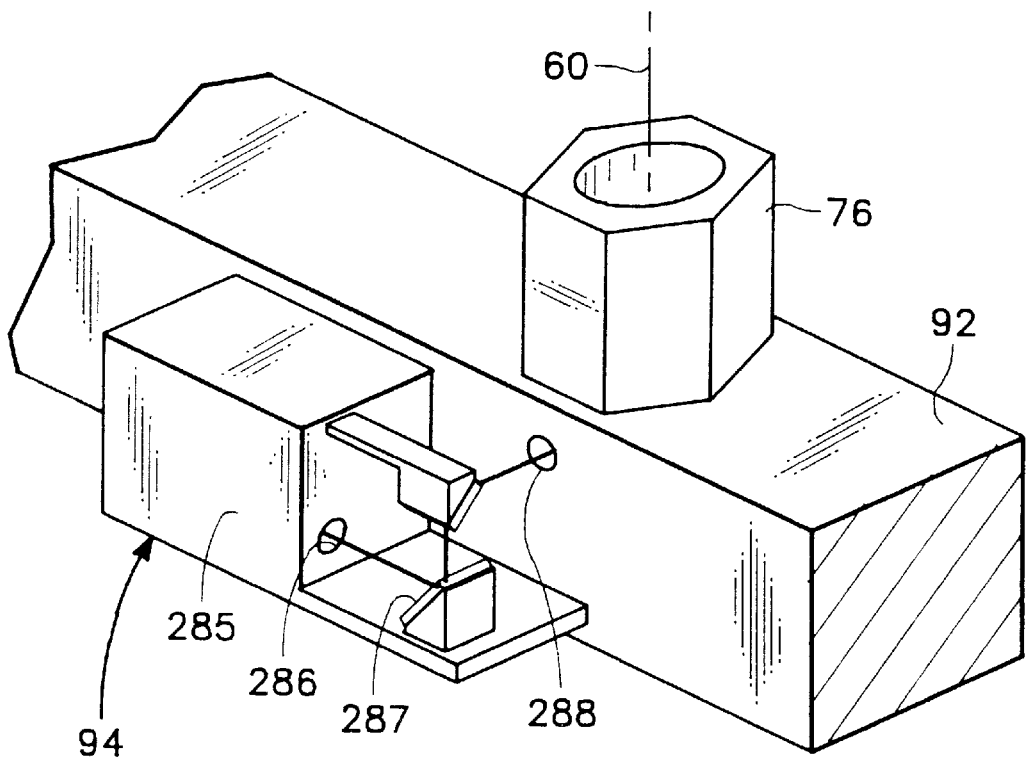
FIG. 15 is a pictorial illustration of the mounting of the dissociation laser upon the spectrometer housing.

The mass spectrometer 90 is contained within the square chamber wall 92, which is machined from a solid block of 6061-T6 aluminum. The rectangular configuration allows easy penetration of feed-throughs and other access through the vacuum wall 92, such as electrical lines and vacuum gauges. The rugged construction allows the Nd:YAG dissociation laser 94 to be mounted directly to the chamber wall 92, as illustrated in FIG. 15, so that optical alignment is easily maintained. One such Nd:YAG laser is the Minilight I, available form Continuum in Santa Clara, Calif. When operating at 266 nm, it produces 5 ns optical pulses and generates 1 mJ per pulse. When focused to a 400:m spot size, a power density of about $10^8 J/cm^2$ is achieved. The laser beam penetrates the vacuum chamber through the window 288 in the wall 92. The unscattered portions of the laser pulse exits the vacuum chamber through another window (not shown), where an optical power meter monitors the laser output. Other pulsed lasers, at other wavelengths, may be used so long as the energy and wavelengths are sufficient to desorb and ionize molecules from the particles. Combinations of lasers may be used for the two functions.

The two primary particle detectors 99 may be Micro-Sphere Plates available from El-mul Technologies of Yavne, Israel. They are 70 mm in diameter with 6 mm center holes. They are floated at a high voltage to maintain a field-free region within the flight tube 96, and they are capacitively de-coupled from the detection equipment, which records the time plots of electrical current from the detectors 99.

It should be appreciated from the foregoing description that the portable analyzer of the invention incorporates several features facilitating its use as a field instrument. A dual-beam laser system positioned along the path of a particle beam incorporates special optical detectors for efficiently detecting light scattered from the particles, to accurately measure particle speed, and a high-intensity laser is controlled to emit light pulses to desorb the particles into their constituent molecules. A compact bipolar mass spectrometer incorporating specially mounted ring electrodes then provides a mass-to change spectrum of the desorbed molecules.

Although the invention has been described in detail with reference only to the preferred embodiment, those skilled in the art will appreciate that various modifications can be made without departing from the invention. Accordingly, the invention is defined only by the following claims.

What is claimed is:

1. A portable analyzer system for determining the size and chemical composition of an aerosol, comprising:

a rigid housing defining a vacuum chamber;

an aerosol interface rigidly mounted on the housing and including a nozzle and one or more skimmers configured to produce a stream of aerosol particles moving along a beam axis at velocities inversely related to their aerodynamic sizes;

a tracking system rigidly mounted on the housing and incorporating first and second light probes positioned at spaced locations along the beam axis, each light probe irradiating a separate probe position along the beam axis and detecting light scattered from that probe position;

a timing circuit receiving signals from the first and second light probes and producing a first output signal indicative of the speed of a particle traveling between the two probe positions and a second signal indicative of the anticipated time when the particle will arrive at a downstream dissociation position located on the beam axis, within the vacuum chamber;

a laser rigidly mounted on the housing and configured to be triggered by the second signal to direct a high-intensity laser beam toward the dissociation position, to dissociate the particle into constituent ions; and a mass spectrometer located within the vacuum chamber and configured to detect the chemical composition of the particle's dissociated constituent ions;

wherein the rigid mountings of the aerosol interface, the tracking system, and the laser on the housing ensure that the elements remain properly aligned relative to each other despite the occurrence of substantial external forces and vibrations.

2. The portable analyzer system of claim 1, wherein the mass spectrometer is a coaxial reflectron time-of-flight mass spectrometer.

3. The portable analyzer system of claim 2, wherein the mass spectrometer is a dual, bipolar coaxial reflectron time-of-flight mass spectrometer.

4. The portable analyzer system of claim 2, wherein the mass spectrometer includes a reflectron comprising a plurality of ring electrodes, at least three plastic rods having recesses receiving a periphery of each of the ring electrodes, and a metal chamber having a wall with partial circular grooves closely fitting the rods.

5. The portable analyzer system of claim 1, wherein the mass spectrometer comprises:

an ion source at least one electrode for imparting kinetic energy to an ion from the ion source;

a flight tube along which the ion travels in a substantially field-free region;

a particle detector disposed at a first end of the flight tube, adjacent to the ion source; and a reflectron disposed at a second end of the flight tube and including a metal inner housing having at least three partial circular axial grooves formed in an inner surface thereof, at least three elastic insulating rods located in the axial grooves, each rod including a plurality of recesses formed into its side, and a plurality of ring electrodes, each located in the recesses of the rods.

6. The portable analyzer system of claim 1, wherein the aerosol interface further includes:

a stage having a bore therethrough along an axis;

a tube movable within the bore, along the axis;

a nozzle mounted on a first end of the tube, the tube being movable to expose the nozzle on a first end of the bore; and a ball valve having a passage therethrough and disposed in a middle portion of the bore, wherein the ball valve is rotatable between a first position, in which its passage is not aligned with the bore, and the bore is blocked, and a second position, in which its passage is aligned with the bore, and the tube and nozzle are allowed to pass through the bore and passage.

7. The portable analyzer system of claim 1, wherein the tracking system further includes:

a tracking system housing defining a vacuum chamber that communicates with the vacuum chamber of the rigid housing and that encompasses the beam axis;

the tracking system housing is configured with first and second apertures sized to receive the first and second light probes; and the first and second light probes each include a light detector module insertable into the respective first and second apertures, wherein each light detector module comprises a body defining an ellipsoidal mirror surface, and a light detector attached to the body and including a mechanical register surface that positions the body relative to the tracking system housing, such that a first focal point of the ellipsoidal mirror surface intersects the beam axis.

8. The portable analyzer system of claim 1, wherein the mass spectrometer comprises:

a reflectron located at an end of the ion path spaced from the ion source and including a plurality of insulating rods located in prescribed positions spaced from the ion path, each rod including a plurality of recesses formed in its side facing the ion path, and a plurality of ring electrodes, each supported by a separate set of recesses formed in the plurality of insulating rods, wherein the ring electrodes include central apertures aligned with the ion path, wherein the reflectron is conditioned to interact with the ions traveling along the ion path and to redirect the ions in a substantially opposite direction; and a particle detector positioned to detect the ions redirected by the reflectron.

9. A portable analyzer system as defined in claim 8, wherein the reflectron further comprises a metallic inner housing disposed around the plurality of insulating rods and the plurality of ring electrodes, the inner housing being configured to support the plurality of insulating rods in their prescribed positions.

10. A portable analyzer system as defined in claim 9, wherein:

the plurality of insulating rods each have uniform circular cross-sections; and the inner housing has an inner wall configured with a plurality of partial circular axial grooves sized to receive and retain the plurality of insulating rods.

11. A portable analyzer system as defined in claim 10, wherein the reflectron comprises four insulating rods spaced uniformly around the ion path.

12. A portable analyzer system as defined in claim 9, wherein the reflectron further comprises a plurality of electrically insulating mounts that support the inner housing within the outer housing.

13. A portable analyzer system as defined in claim 12, wherein:

the plurality of mounts define a spherical joint; and the metallic inner housing is configured to be movably adjustable within the mounts, to facilitate alignment of the plurality of ring electrodes relative to the ion path.

14. A rugged, coaxial time-of-flight spectrometer, comprising:

an ion source;

at least one electrode for imparting kinetic energy to an ion from the ion source;

a flight tube along which the ion travels in a substantially field-free region;

a particle detector disposed at a first end of the flight tube, adjacent to the ion source; and a reflectron disposed at a second end of the flight tube and including a metal inner housing having at least three partial circular axial grooves formed in an inner surface thereof, at least three elastic insulating rods located in the axial grooves, each rod including a plurality of recesses formed into its side, and a plurality of ring electrodes, each located in the recesses of the rods.

15. The coaxial time-of-flight spectrometer of claim 14, wherein:

the inner housing includes a cylindrical side wall; and the spectrometer further includes a rectangular outer housing and a plurality electrically insulating mounts supporting the inner housing.

16. The coaxial time-of-flight spectrometer of claim 15, wherein some of the mounts form a spherical joint.

17. An aerosol interface for an aerosol analyzer, comprising:

a stage having a bore therethrough along an axis;

a tube movable within the bore, along the axis;

a nozzle mounted on a first end of the tube, the tube being movable to expose the nozzle on a first end of the bore and to remove the nozzle from a second end of the bore; and a ball valve having a passage therethrough and disposed in a middle portion of the bore, wherein the ball valve is rotatable between a first position, in which its passage is not aligned with the bore, and the bore is blocked, and a second position, in which its passage is aligned with the bore, and the tube and nozzle are allowed to pass through the bore and passage.

18. The aerosol interface of claim 17, and further comprising:

at least one skimmer having an aperture arranged along the axis; and a vacuum system for creating a differential pressure across the nozzle and the at least one skimmer.

19. A rugged, coaxial, reflectron time-of-flight mass spectrometer, comprising:

an outer housing defining a vacuum chamber;

an ion source located within the vacuum chamber;

at least one electrode located within the vacuum chamber, for imparting kinetic energy to a succession of ions from the ion source and thereby directing the ions along an ion path within the vacuum chamber;

a reflectron located within the vacuum chamber, at an end of the ion path spaced from the ion source, wherein the reflectron includes a plurality of insulating rods located in prescribed positions spaced from the ion path, each rod including a plurality of recesses formed in its side facing the ion path, and a plurality of ring electrodes, each supported by a separate set of recesses formed in the plurality of insulating rods, wherein the ring electrodes include central apertures aligned with the ion path, wherein the reflectron is conditioned to interact with the ions traveling along the ion path and to redirect the ions in a substantially opposite direction; and a particle detector positioned to detect the ions redirected by the reflection.

20. A time-of-flight mass spectrometer as defined in claim 19, wherein the reflectron further comprises a metallic inner housing disposed around the plurality of insulating rods and the plurality of ring electrodes, the inner housing being configured to support the plurality of insulating rods in their prescribed positions.

21. A time-of-flight mass spectrometer as defined in claim 20, wherein:

the plurality of insulating rods each have uniform circular cross-sections; and the inner housing has an inner wall configured to have a plurality of partial circular axial grooves sized to receive and retain the plurality of insulating rods.

22. A time-of-flight mass spectrometer as defined in claim 21, wherein the reflectron comprises four insulating rods spaced uniformly around the ion path.

23. A time-of-flight mass spectrometer as defined in claim 20, and further comprising a plurality of electrically insulating mounts that support the inner housing within the outer housing.

24. A time-of-flight mass spectrometer as defined in claim 23, wherein:

the plurality of mounts define a spherical joint; and the metallic inner housing is configured to be movably adjustable within the mounts, to facilitate alignment of the plurality of ring electrodes relative to the ion path.

25. A rugged, coaxial, reflectron time-of-flight mass spectrometer, comprising:

an outer housing defining a vacuum chamber;

an ion source located within the vacuum chamber;

at least one electrode located within the vacuum chamber, for imparting kinetic energy to a succession of ions from the ion source and thereby directing the ions along an ion path within a field-free region of the vacuum chamber;

a reflectron located within the vacuum chamber, at an end of the ion path, wherein the reflectron is conditioned to interact with the ions traveling along the ion path and to redirect the ions in a substantially opposite direction; and a particle detector positioned to detect the ions redirected by the reflectron; and a plurality of electrically insulating mounts that support the reflectron within the outer housing, the mounts defining a spherical joint, wherein the reflectron is configured to be movably adjustable within the mounts, to facilitate alignment of the reflectron relative to the ion path.

26. A time-of-flight mass spectrometer as defined in claim 25, wherein the reflectron comprises:

a plurality of insulating rods located in prescribed positions spaced from the ion path, each rod including a plurality of recesses formed in its side facing the ion path;

a plurality of ring electrodes, each supported by a separate set of recesses formed in the plurality of insulating rods, wherein the ring electrodes include central apertures aligned with the ion path; and a metallic inner housing that encloses the plurality of insulating rods and the plurality of ring electrodes and that is configured to support the plurality of insulating rods in their prescribed positions.

27. A time-of-flight mass spectrometer as defined in claim 26, wherein:

the plurality of insulating rods each have uniform circular cross-sections; and the inner housing has an inner wall configured to have a plurality of partial circular axial grooves sized to receive and retain the plurality of insulating rods.

* * * * *